United States Patent [19]

Urano et al.

[11] Patent Number: 5,677,112

[45] Date of Patent: Oct. 14, 1997

[54] PROCESS FOR FORMING A PATTERN ON A SEMICONDUCTOR SUBSTRATE USING A DEEP ULTRAVIOLET ABSORBENT COMPOSITION

[75] Inventors: Fumiyoshi Urano; Keiji Oono; Hiroshi Matsuda, all of Kawagoe; Masayuki Endo, Izumi; Satoshi Kobayashi, Kadoma, all of Japan

[73] Assignees: Wako Pure Chemical Industries, Ltd.; Matsushita Electric Industries Co., Ltd., both of Osaka, Japan

[21] Appl. No.: 687,989

[22] Filed: Jul. 29, 1996

Related U.S. Application Data

[62] Division of Ser. No. 272,752, Jul. 11, 1994, Pat. No. 5,576,359.

[30] Foreign Application Priority Data

Jul. 20, 1993 [JP] Japan ................................ 5-200417
Apr. 1, 1994 [JP] Japan ................................ 6-087770

[51] Int. Cl.$^6$ .................................................. G03C 5/00
[52] U.S. Cl. .................... 430/325; 430/270.1; 430/280.1; 430/330
[58] Field of Search ......................... 430/325, 280.1, 430/270.1, 330, 926; 523/400, 456

[56] References Cited

U.S. PATENT DOCUMENTS

| | | | |
|---|---|---|---|
| 4,007,271 | 2/1977 | Robertson | 514/163 |
| 4,413,052 | 11/1983 | Green et al. | 430/327 |
| 4,843,097 | 6/1989 | Shroot et al. | 514/680 |

FOREIGN PATENT DOCUMENTS

| | | |
|---|---|---|
| 0 233 056 | 8/1987 | European Pat. Off. . |
| 0 542 008 A1 | 5/1993 | European Pat. Off. . |
| 2257442 | 11/1972 | Germany . |
| 3642247 | 6/1987 | Germany . |
| 59-93448 | 5/1984 | Japan . |
| 59-135748 | 8/1984 | Japan . |
| 4-298505 | 10/1992 | Japan . |
| 5-47656 | 2/1993 | Japan . |
| 5-222153 | 8/1993 | Japan . |

OTHER PUBLICATIONS

J. Chem. Soc. (C), The Formation of Chromonone–type Systems via the Acylation of Derivatives of 2,6–Dihydroxyanthracene, by D.W. Cameron et al., Univ. Chemical Laboratory, Cambridge, 1967.

Primary Examiner—George F. Lesmes
Assistant Examiner—Laura Weiner
Attorney, Agent, or Firm—Armstrong, Westerman, Hattori, McLeland & Naughton

[57] ABSTRACT

A deep ultraviolet absorbent comprising at least one compound having one or more glycidyl groups in the molecule and at least one anthracene derivative, and a solvent capable of dissolving these compounds is effective for preventing reflection of deep ultraviolet light from a substrate during formation of resist pattern, resulting in forming ultra-fine patterns without causing notching and halation.

4 Claims, 4 Drawing Sheets

PROCESS FOR FORMING A PATTERN ON A SEMICONDUCTOR SUBSTRATE USING A DEEP ULTRAVIOLET ABSORBENT COMPOSITION

This is a divisional of application Ser. No. 08/272,752 filed Jul. 11, 1994, now U.S. Pat. No. 5,576,359.

BACKGROUND OF THE INVENTION

The present invention relates to a method for forming resist patterns in production of semiconductor devices. More particularly, the invention pertains to a deep ultraviolet absorbent used for eliminating or minimizing influence of reflected light from the substrate when forming a resist pattern on a semiconductor substrate by lithography using deep ultraviolet light, and a pattern forming method using such a deep ultraviolet absorbent.

With a recent trend toward high-density integration of semiconductor devices, there has been rising call for shortening of wavelength of the energy source of exposure methods used for fine working, particularly photolithography, and now use of deep ultraviolet. light (300 nm or less in wavelength), KrF excimer laser light (248.4 nm), ArF excimer laser light (193 nm), electron beams and soft X-rays is seriously considered. Higher sensitivity and higher resolution of resist material has been required in use of such energy source, and as an answer to such request, a chemically amplified resist material using an acid generated by exposure as medium has been proposed [H. Ito et al: Polym. Eng. Sci., Vol. 23, p. 1012, 1983]. Since then, significant advancements have been made, with many reports published, on the chemically amplified resist material, and at present there is available a resist material having a resolving capability on the order of 0.25–0.30 μm. Generally, use of a chemically amplified resist on a flat silicon substrate provides a good resist pattern with a rectangular sectional shape. However, poly(hydroxystyrene) popularly used as base resin for the chemically amplified resist is highly transparent to deep ultraviolet light such as KrF excimer laser light, so that it is highly susceptible to intra-film multiple reflection of deep ultraviolet light such as excimer laser light from the semiconductor substrate. The resist film is varied in thickness under the influence of this intra-film multiple reflection, consequently causing a substantial change of resist pattern dimensions. Especially when the semiconductor substrate is nonuniform in thickness or in the case of a highly reflective substrate such as aluminum substrate, variation of the resist film thickness is large and also intra-film multiple reflection is intensified, giving rise to a problem of excessive variation of resist pattern dimensions or disconnection of the substrate.

Use of an organic anti-reflective film has been proposed as a measure against influence of intra-film multiple reflection. An organic anti-reflective film is usually formed by spin coating a novolak resin/naphthoquinonediazide type resist on a semiconductor substrate and heating the coat at a high temperature.

This method, however, has a problem in that light absorptivity of the novolak resin/naphthoquinonediazide type resist is insufficient and the formed film can not provide a satisfactory anti-reflective effect. Among other reports on anti-reflective film is use of an organic silane compound such as disclosed in JP-A-54-7656.

However, the method using an organic silane compound as anti-reflective film material involves a problem in that silicon oxide is produced from ashing and it can not be removed perfectly. Further, use of polyamide or polyimide or resin containing sulfonyl groups for the anti-reflective film presents the problem of intermixture with the resist material at the interface or footing or undercutting of the pattern because of the acidic or basic atmosphere (e.g. JP-A-62-264051=EP0233056, JP-A-59-93448, etc.).

SUMMARY OF THE INVENTION

The present invention has been made in view of the above circumstances, and it has for its object to provide a novel deep ultraviolet absorbent capable of forming an anti-reflective film on the semiconductor substrate surface, which film is used for the purpose of eliminating influence of intra-film multiple reflection caused by reflection of light from the semiconductor substrate in forming a resist pattern by lithography using deep ultraviolet light such as KrF excimer laser light or ArF excimer laser light, said anti-reflective film being able to comply with the request for mass production, and a pattern forming process using such a deep ultraviolet absorbent.

The present invention provides a deep ultraviolet absorbent comprising at least one compound having one or more glycidyl groups in the molecule, at least one anthracene derivative represented by the following formula:

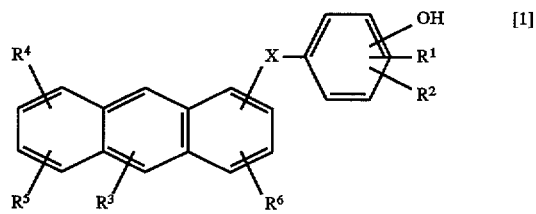

wherein X represents —O—SO$_2$—, —O—CO— or —CO—; $R^1$ and $R^2$ represent independently hydrogen atom, alkyl group, alkoxyl group, halogen atom or hydroxyl group; $R^3$, $R^4$, $R^5$ and $R^6$ represent independently hydrogen atom, alkyl group, alkoxyl group, halogen atom or a group represented by the following formula:

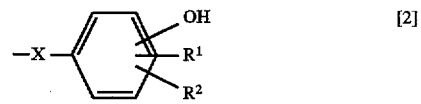

wherein X, $R^1$ and $R^2$ are as defined above; provided that at least one of $R^3$ through $R^6$ is the group of the formula [2], and the group of the formula [2] in number of 3 cannot be positioned at the 1, 8, and 9 positions of the anthracene ring at the same time, and a solvent capable of dissolving said compounds.

The present invention also provides a pattern forming process comprising the steps of (i) coating said deep ultraviolet absorbent on a semiconductor substrate and heating the coat to bring about a crosslinking reaction, thereby forming a film; (ii) coating a resist material on the deep ultraviolet absorbent film formed in the step (i) and baking the coat to form a resist film; (iii) exposing the resist film to KrF excimer laser light or deep ultraviolet light through a mask and then subjecting the exposed film to a heat treatment; and (iv) developing the film with an alkaline developing solution.

The present invention further provides an anthracene derivative of the formula:

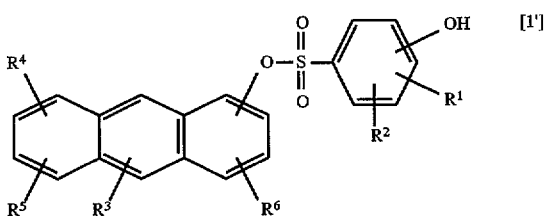

wherein $R^1$ and $R^2$ are independently a hydrogen atom, an alkyl group, an alkoxy group, a halogen atom or a hydroxyl group; $R^3$, $R^4$, $R^5$ and $R^6$ are independently a hydrogen atom, an alkyl group, an alkoxy group, a halogen atom, or a group of the formula:

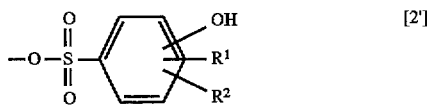

wherein $R^1$ and $R^2$ are as defined above; provided that at least one of $R^3$ through $R^6$ is the group of the formula [2'].

DESCRIPTION OF THE PREFERRED EMBODIMENTS

Figure 1:
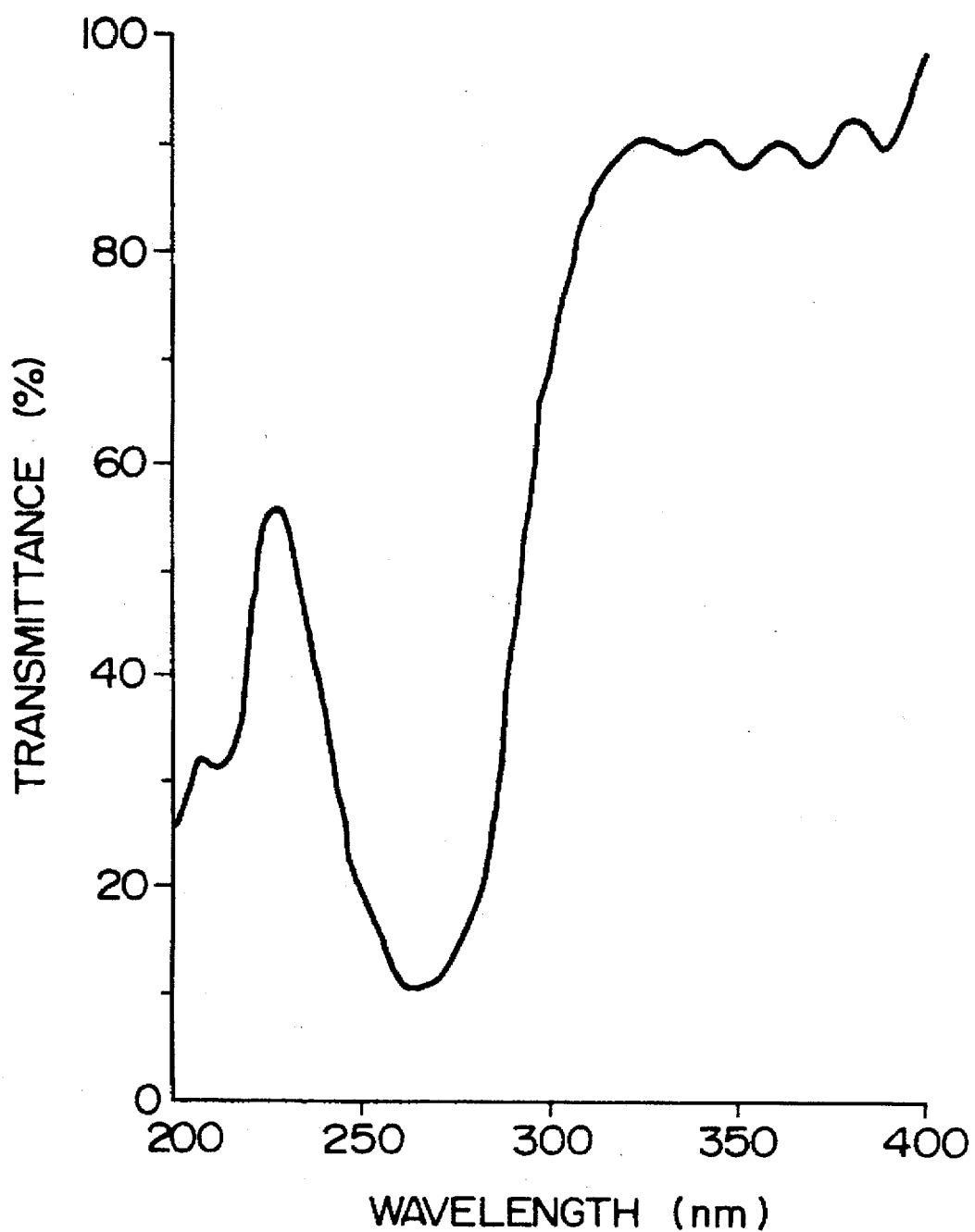
FIG. 1 is an ultraviolet spectrophotometric curve of the deep ultraviolet absorbent film obtained in Example 1.

In the course of studies on the material of anti-reflective film to be formed on the semiconductor substrate surface for the purpose of preventing multiple reflection which is caused in the resist film due to shortened wavelength of applied light and high transparency of base resin in forming a resist pattern by lithography with deep ultraviolet light such as KrF excimer laser light, the present inventors have succeeded in working out a deep ultraviolet absorbent which can meet all of the specified conditions such as excellent controllability of film forming by spin coating, high heat resistance, no possibility of intermixture with resist material at the interface therewith, and high absorption at wavelengths below 300 nm, especially around 248 nm. The present invention has been attained on the basis of this disclosure.

Regarding the component material of the anti-reflective film according to the present invention, it is essential that such component material is capable of absorbing deep ultraviolet light, can contribute to heat resistance of the anti-reflective film and has the property not to intermix with the resist material applied on the film at the interface. In search of a compound that can meet these conditions, the present inventors noticed a series of compounds having in the molecule two or more phenolic hydroxyl groups which are capable of crosslinking reaction with a resin having one or more glycidyl groups on heating and also having in the molecule an anthracene skeleton showing strong absorption at around 220–300 nm, and have successfully worked out the compounds represented by the above-shown formula [1] having an electron attractive group such as carbonyl, carboxyl or sulfonyl group introduced to the p- or m-position of the phenolic hydroxyl group for facilitating said thermal crosslinking reaction.

The anthracene derivative usable in the present invention is represented by the formula:

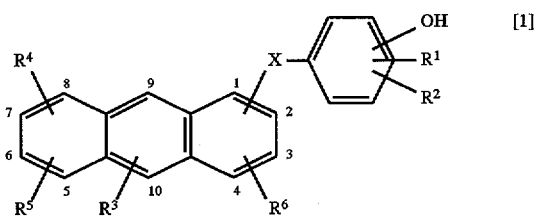

wherein X is —O—$SO_2$—, —O—CO— or —CO—; $R^1$ and $R^2$ are independently a hydrogen atom, a lower alkyl group preferably having 1 to 6 carbon atoms, more preferably 1 to 4 carbon atoms, a lower alkoxy group preferably having 1 to 6 carbon atoms, more preferably 1 to 4 carbon atoms, a halogen atom such as chlorine, bromine and iodine, or a hydroxyl group; $R^3$, $R^4$, $R^5$ and $R^6$ are independently a hydrogen atom, a lower alkyl group preferably having 1 to 6 carbon atoms, more preferably 1 to 4 carbon atoms, a lower alkoxy group preferably having 1 to 6 carbon atoms, more preferably 1 to 4 carbon atoms, a halogen atom such as chlorine, bromine or iodine, or a group of the formula:

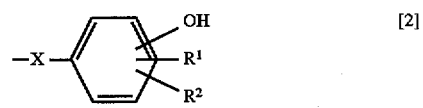

wherein X, $R^1$ and $R^2$ are as defined above; one or more hydroxyl groups being preferably positioned at para and/or meta positions with regard to X, provided that at least one of $R^3$ through $R^6$ is the group of the formula and the group of the formula [2] in number of 3 cannot be positioned at the 1, 8 and 9 positions of the anthracene ring at the same time. Among the compound of the formula [1], those represented by the formula:

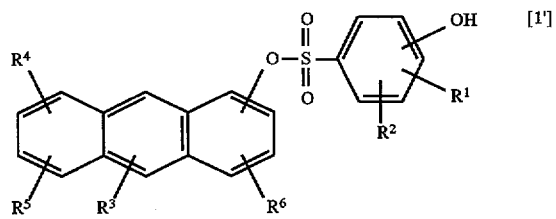

wherein $R^1$ and $R^2$ are independently a hydrogen atom, an alkyl group, an alkoxy group, a halogen atom or a hydroxyl group; $R^3$, $R^4$, $R^5$ and $R^6$ are independently a hydrogen atom, an alkyl group, an alkoxy group, a halogen atom, or the group of the formula [2']:

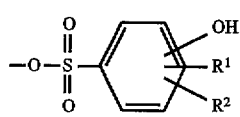

wherein $R^1$ and $R^2$ are as defined above; one or more hydroxyl groups being preferably positioned at para and/or meta positons with regard to X, provided that at least one of $R^3$ through $R^6$ is the group of the formula [2'].

In the compounds of the formulae [1] and [1'], when the group of the formula [2] or [2'] in number of 3 is positioned at the 1, 8 and 9 positions of the anthracene ring at the same time, the resulting compounds do not bring about crosslinking reaction with a compound (or resin) having one or more glycidyl groups, resulting in failing to form a desirable antireflection coating. Further, when one or more phenolic hydroxyl groups are positioned at para and/or meta positions with regard to X or —O—$SO_2$— group in the formula [1] or [1'], crosslinking reaction with a compound (or resin) having one or more glycidyl groups is remarkably increased to give a desirable antireflection coating.

The compounds represented by the formula [1] can be easily synthesized by, for example, the following method (a), (b) or (c).

(a) Method 1

In the case of a compound of the formula [1] wherein $R^3$ is a group of the formula [2], $R^4$, $R^5$ and $R^6$ are each hydrogen atom, alkyl group, halogen atom or a group of the formula [2] and X is carbonyloxy group or sulfonyloxy group, it can be easily synthesized according to the following reaction scheme 1:

<Reaction scheme 1>

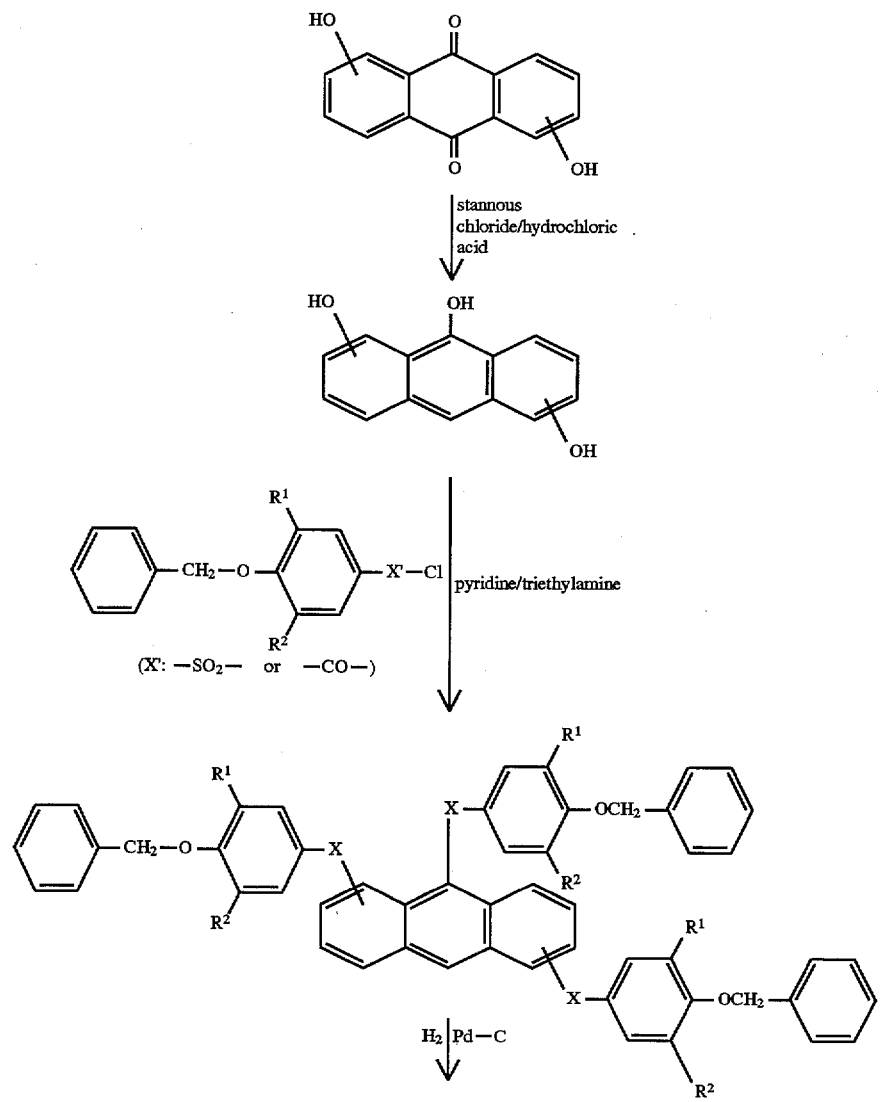

-continued
<Reaction scheme 1>

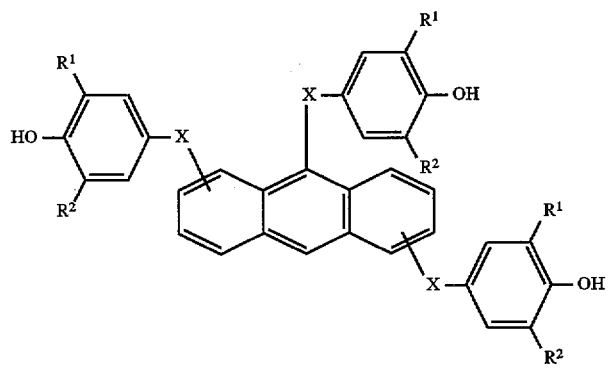

In the above reaction, first an anthraquinone derivative having at least one hydroxyl group is dissolved in 5-20 times by much volume of acetic acid or propionic acid, followed by addition of excess amounts of concentrated hydrochloric acid and stannous chloride to carry out a reducing reaction at 10° to 120° C. to form an anthracenetriol derivative.

This anthracenetriol derivative is reacted with twice the molar quantity or more (3 moles in the reaction scheme 1) of p-benzyloxybenzoyl chloride or p-benzyloxybenzenesulfonyl chloride in the presence of twice the molar quantity or more (3 moles in the reaction scheme 1) of a base (e.g. triethylamine, piperidine, NaOH, KOH, NaH or the like) in 1-20 times as much volume of an appropriate organic solvent (e.g. triethylamine, pyridine, methylene chloride, toluene, ethyl ether, tetrahydrofuran or the like) at 0°-150° C. for 30 minutes to 20 hours to give an objective compound wherein the hydroxyl group is protected (benzyl group in the case of the reaction scheme 1).

This compound is then subjected to hydrogenation reaction in 1-20 times as much volume of an appropriate organic solvent (e.g. methanol, ethanol, propanol, isopropanol, tetrahydrofuran, methylene chloride, chloroform or the like) in the presence of a catalyst such as Raney nickel, palladium on carbon or the like under normal pressure to 50 kg/cm² (initial hydrogen pressure) at 0°-50° C. for 1-10 hours to give an objective compound of the formula [1].

(b) Method 2

In the case of a compound of the formula [1] wherein $R^3$ is hydrogen atom, $R^4$ or $R^6$ is a group represented by the formula [2], $R^6$ or $R^4$ and $R^5$ are hydrogen atom, alkyl group or halogen atom, and X is carbonyloxy group or sulfonyloxy group, it can be synthesized according to the following reaction scheme 2:

<Reaction scheme 2>

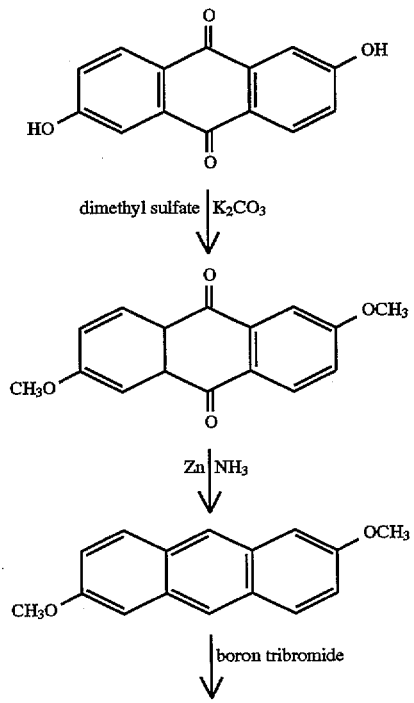

-continued
<Reaction scheme 2>

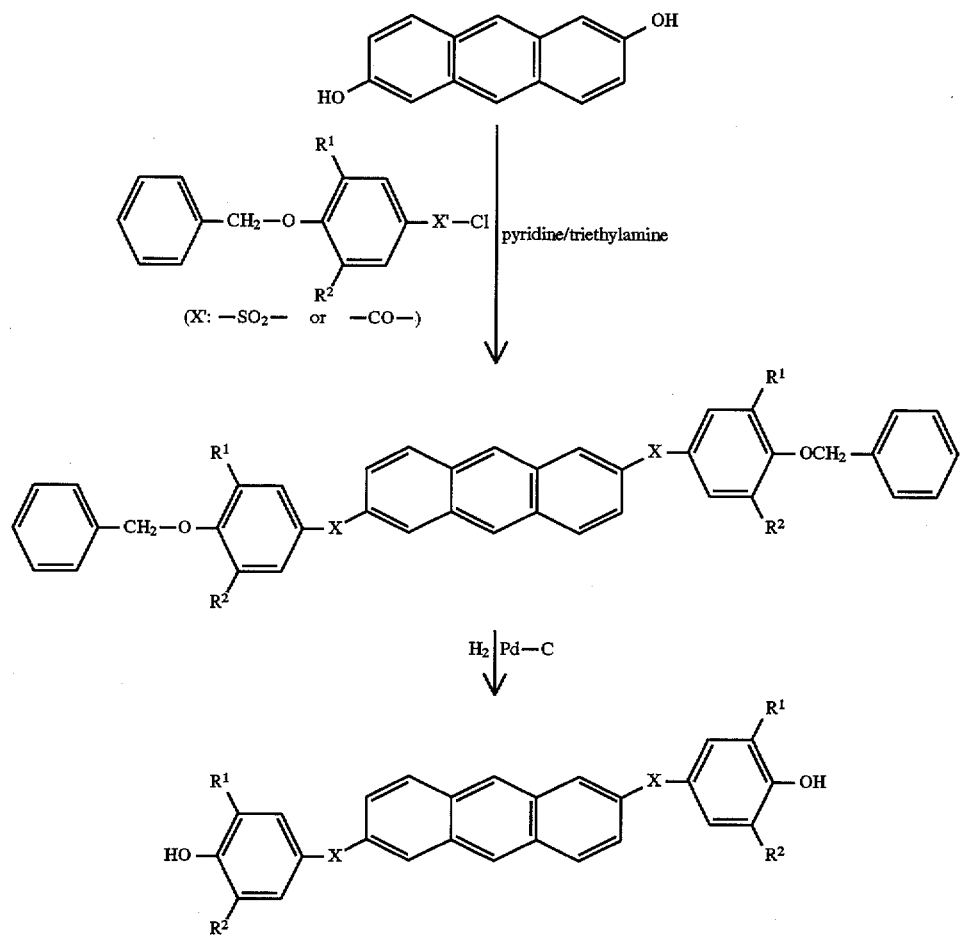

An anthraquinone derivative having 2 hydroxyl groups, for example, 2,6-dihydroxyanthraquinone, is reacted with an alkylating agent such as dimethyl sulfate, in the presence of a base such as anhydrous potassium carbonate, etc. to protect the hydroxyl groups, and then reduced with zinc/ammonia water to give, for example, 2,6-dimethoxyanthracene having the protected hydroxyl groups at the 2,6-positions. Then the protective group of this hydroxyl group is eliminated by reaction with, for example, boron tribromide to form 2,6-dihydroxyanthracene. This is esterified with p-benzyloxybenzoyl chloride or p-benzyloxybenzenesulfonyl chloride and subjected to hydrogenation reaction to eliminate the protective group (benzyl group) in the same way as in the above-described method (a) to give a compound of the formula [1].

(c) Method 3

In the case of a compound of the formula [1] wherein $R^3$ is hydrogen atom, $R^4$ and $R^6$ are a group represented by the formula [2], $R^5$ is hydrogen atom, alkyl group, halogen atom or a group represented by the formula [2], and X is carbonyloxy group or sulfonyloxy group, it can be synthesized according to the following reaction scheme 3:

<Reaction scheme 3>

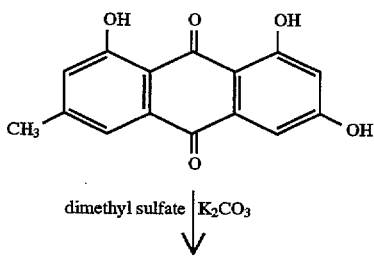

-continued
<Reaction scheme 3>

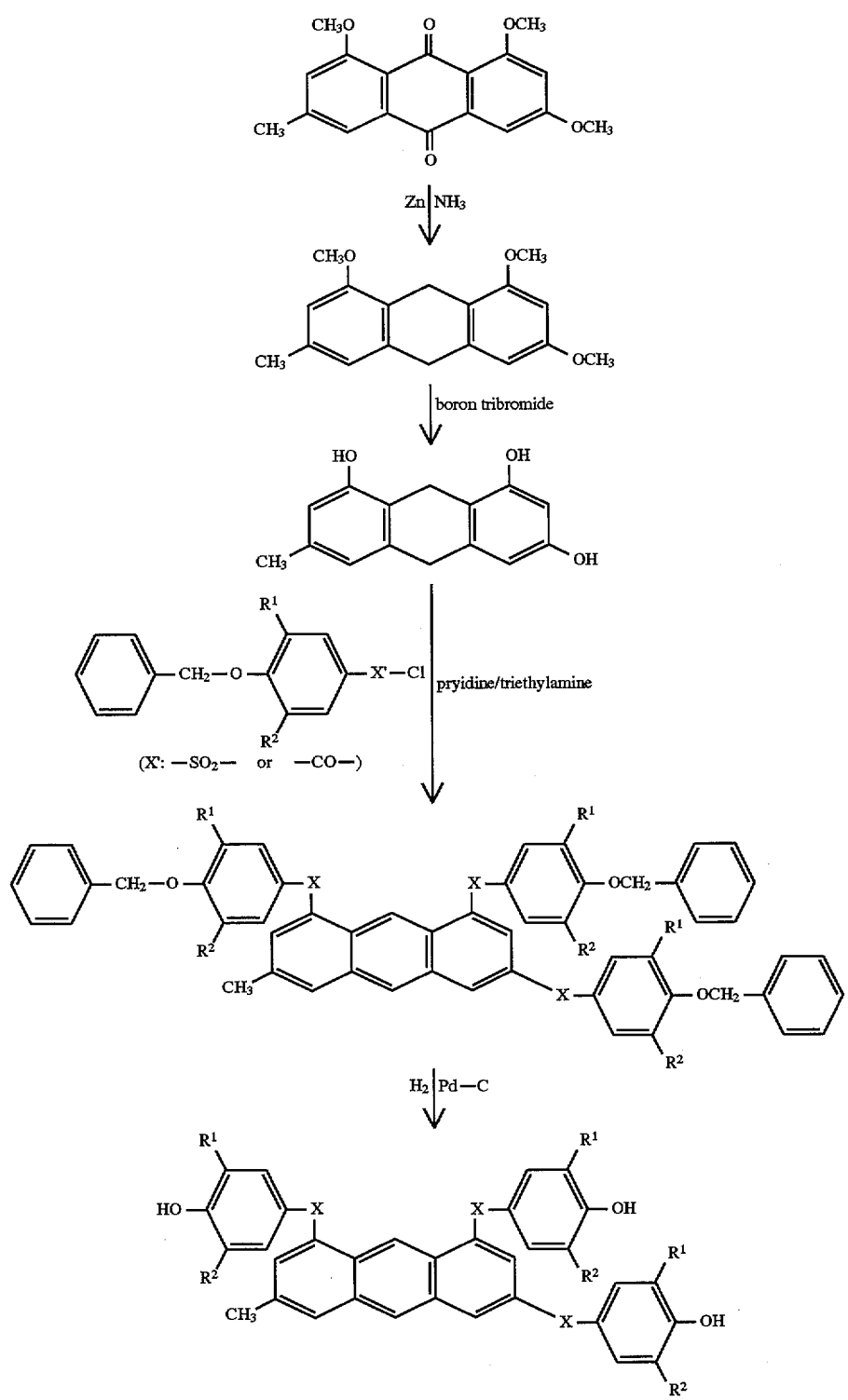

An anthraquinone derivative having 3 or more hydroxyl groups, for example, 6-methyl-1,3,8-trihydroxy anthraquinone, is reacted according to the above-described method (b) to effect alkyl etherification of the hydroxyl groups and then reduced with zinc/ammonia water to give, for example, 6-methyl-1,3,8-trimethoxyanthracene having the protected hydroxyl groups at the 1,3,8-positions. Then the protective group n of this hydroxyl group is eliminated by reaction with, for example, boron tribromide to form 6-methyl-1,3,8-trihydroxyanthracene. This is esterified with p-benzyloxybenzoyl chloride or p-benzyloxybenzenesulfonyl chloride and then the protective group (benzyl group) of the hydroxyl group is eliminated by catalytic reduction or other means to give an objective compound of the formula [1].

The following are the examples of the compounds represented by the formula [1] (which may hereinafter be called crosslinking agent according to the present invention):
2,6,9-tris(4-hydroxybenzoyloxy)anthracene,
2,6,9-tris(3,4-dihydroxybenzoyloxy)anthracene,
2,6,9-tris(3-hydroxybenzoyloxy)anthracene,
2,6,9-tris(4-hydroxy-3-methoxybenzoyloxy)anthracene,
2,6,9-tris(3-chloro-4-hydroxybenzoyloxy)anthracene,
2,6,9-tris(3-hydroxy-4-methylbenzoyloxy)anthracene,
1,2,10-tris(4-hydroxybenzoyloxy)anthracene,
1,2-10-tris(3-hydroxybenzoyloxy)anthracene,
1,2,10-tris(3,4-dihydroxybenzoyloxy)anthracene,
1,2,10-tris(4-hydroxy-3-methoxybenzoyloxy)anthracene,
1,2,10-tris(3-hydroxy-4-methylbenzoyloxy)anthracene,
1,2,10-tris(3-chloro-4-hydroxybenzoyloxy)anthracene,
1,5,9-tris(4-hydroxybenzoyloxy)anthracene,
1,5,9-tris(3-hydroxybenzoyloxy)anthracene,
1,5,9-tris(3,4-dihydroxybenzoyloxy)anthracene,
1,5,9-tris(4-hydroxy-3-methoxybenzoyloxy)anthracene,
1,5,9-tris(3-hydroxy-4-methylbenzoyloxy)anthracene,
1,5,9-tris(3-chloro-4-hydroxybenzoyloxy)anthracene,
1,4,9-tris(4-hydroxybenzoyloxy)anthracene,
1,5-bis(4-hydroxybenzoyloxy)anthracene,
1,5-bis(3-hydroxybenzoyloxy)anthracene,
1,5-bis(3,4-dihydroxybenzoyloxy)anthracene,
1,5-bis(4-hydroxy-3-methoxybenzoyloxy)anthracene,
1,5-bis(3-chloro-4-hydroxybenzoyloxy)anthracene,
1,5-bis(3-hydroxy-4-methylbenzoyloxy)anthracene,
2,6-bis(4-hydroxybenzoyloxy)anthracene,
2,6-bis(3-hydroxybenzoyloxy)anthracene,
2,6-bis(3,4-dihydroxybenzoyloxy)anthracene,
2,6-bis(4-hydroxy-3-methoxybenzoyloxy)anthracene,
2,6-bis(3-chloro-4-hydroxybenzoyloxy)anthracene,
2,6-bis(3-hydroxy-4-methylbenzoyloxy)anthracene,
1,2-bis(4-hydroxybenzoyloxy)anthracene,
1,2-bis(4-hydroxy-3-methoxybenzoyloxy)anthracene,
1,8-bis(4-hydroxybenzoyloxy)anthracene,
1,8-bis(4-hydroxy-3-methoxybenzoyloxy)anthracene,
1,8-bis(4-hydroxybenzoyloxy)-3-methylanthracene,
6,7-dichloro-1,4-bis(3,4-dihydroxybenzoyloxy)anthracene,
6-methyl-1,3,8-tris(4-hydroxybenzoyloxy)anthracene,
1,4-bis(4-hydroxybenzoyloxy)anthracene,
6-methyl-1,3,8,10-tetra(4-hydroxybenzoyloxy)anthracene,
1,10-bis(4-hydroxybenzoyloxy)-2-methoxyanthracene,
2,6-bis(4-hydroxybenzoyloxy)-9-methoxyanthracene,
2,3-dimethyl-1,4,9-tris(4-hydroxybenzoyloxy)anthracene,
1,4-bis(3,4-dihydroxybenzoyloxy)anthracene,
1,2,5,8-tetra(4-hydroxybenzoyloxy)anthracene,
5,8-dichloro-1,4,9-tris(4-hydroxybenzoyloxy)anthracene,
2,6,9-tris(4-hydroxybenzenesulfonyloxy)anthracene,
2,6,9-tris(3-hydroxybenzenesulfonyloxy)anthracene,
2,6,9-tris(3,4-dihydroxybenzenesulfonyloxy)anthracene,
2,6,9-tris(4-hydroxy-3-methoxybenzenesulfonyloxy) anthracene,
2,6,9-tris(3-chloro-4-hydroxybenzenesulfonyloxy)- anthracene,
2,6,9-tris(3-hydroxy-4-methylbenzenesulfonyloxy) anthracene,
1,2,10-tris(4-hydroxybenzenesulfonyloxy)anthracene,
1,2,10-tris(3-hydroxybenzenesulfonyloxy)anthracene,
1,2,10-tris(3,4-dihydroxybenzenesulfonyloxy)anthracene,
1,2,10-tris(4-hydroxy-3-methoxybenzenesulfonyloxy) anthracene,
1,2,10-tris(3-chloro-4-hydroxybenzenesulfonyloxy) anthracene,
1,2,10-tris(3-hydroxy-4-methylbenzenesulfonyloxy) anthracene,
1,5,9-tris(4-hydroxybenzenesulfonyloxy)anthracene,
1,5,9-tris(3-hydroxybenzenesulfonyloxy)anthracene,
1,5,9-tris(3,4-dihydroxybenzenesulfonyloxy)anthracene,
1,5,9-tris(4-hydroxy-3-methoxybenzenesulfonyloxy) anthracene,
1,5,9-tris(3-chloro-4-hydroxybenzenesulfonyloxy) anthracene,
1,5,9-tris(3-hydroxy-4-methylbenzenesulfonyloxy) anthracene,
1,4,9-tris(4-hydroxybenzenesulfonyloxy)anthracene,
1,5-bis(4-hydroxybenzenesulfonyloxy)anthracene,
1,5-bis(3-hydroxybenzenesulfonyloxy)anthracene,
1,5-bis(3,4-dihydroxybenzenesulfonyloxy)anthracene,
1,5-bis(4-hydroxy-3-methoxybenzenesulfonyloxy) anthracene,
1,5-bis(3-hydroxy-4-methylbenzenesulfonyloxy) anthracene,
1,5-bis(3-chloro-4-hydroxybenzenesulfonyloxy)anthracene,
2,6-bis(4-hydroxybenzenesulfonyloxy)anthracene,
2,6-bis(3-hydroxybenzenesulfonyloxy)anthracene,
2,6-bis(3,4-dihydroxybenzenesulfonyloxy)anthracene,
2,6-bis(4-hydroxy-3-methoxybenzenesulfonyloxy) anthracene,
2,6-bis(3-hydroxy-4-methylbenzenesulfonyloxy) anthracene,
2,6-bis(3-choro-4-hydroxybenzenesulfonyloxy)anthracene,
2,6-bis(4-hydroxybenzenesulfonyloxy)-9-ethoxyanthracene,
2,6-bis(4-hydroxybenzoyloxy)-9-(4-hydroxybenzoyl) anthracene,
2,6-bis(4-hydroxybenzoyloxy)-9-(4-hydroxybenzenesulfonyl)anthracene,
1,2-bis(4-hydroxybenzenesulfonyloxy)anthracene,
1,8-bis(4-hydroxy-3-methoxybenzenesulfonyloxy) anthracene, and
1,4-bis(4-hydroxybenzenesulfonyloxy)anthracene.

The deep ultraviolet absorbent of the present invention contains, in addition to at least one crosslinking agent according to this invention, at least one compound having one or more glycidyl groups in the molecule.

The compound having one or more glycidyl groups in the molecule used in the present invention may be any of those having excellent film forming properties and capable of crosslinking reaction with the co-existing crosslinking agent on heating to form a heat-resistant resin. Examples of such compounds include polyethylene or polypropylene glycol diglycidyl ethers represented by the following formula [3]:

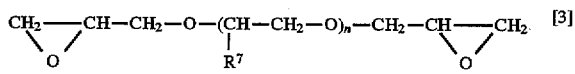

(wherein $R^7$ is hydrogen atom or methyl group; and n is an integer of 1 to 13), sorbitol polyglycidyl ethers represented by the following formula [4]:

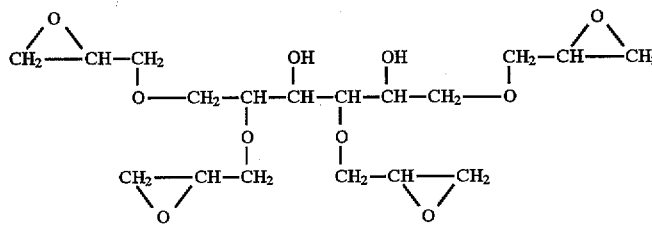

[4]

sorbitol polyglycidyl ether resins represented by the following formula [5]:

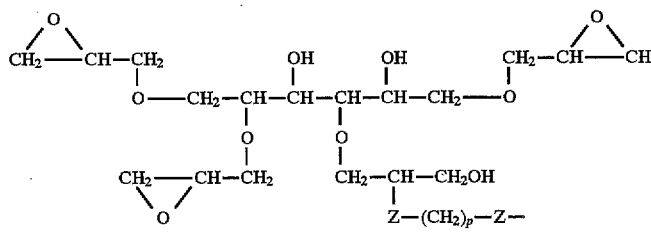

[5]

(wherein Z is —NH— or —COO—; and p is an integer of 1 to 10) and the resins represented by the following formula [6]:

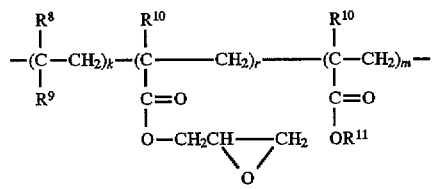

[6]

wherein $R^8$ and $R^{10}$ represent independently hydrogen atom or methyl group; $R^9$ represents hydroxyl group or —$COOR^{12}$ ($R^{12}$ being $C_{1-6}$ alkyl group); $R^{11}$ represents hydrogen atom, $C_{1-6}$ alkyl group (different from the alkyl group of $R^{12}$), norbornyl group, adamantyl group, 9-anthracenemethyl group, 2,3-dihydroxypropyl group or 2-hydroxyethyl group; k and r are an integer of 1 or more, provided that r/(k+r)=0.1–0.9; and m is 0 or an integer of 1 or more, provided that m/(k+r+m)=0–0.5.

Among the above-cited compounds having one or more glycidyl groups in the molecule, polypropylene glycol diglycidyl ethers, polyethylene glycol diglycidyl ethers and sorbitol polyglycidyl ethers are easily available as commercial products, and the resins represented by the formula [5] can be easily obtained by thermally reacting a sorbitol polyglycidyl ether with an alkylenedicarboxylic acid or alkylenediamine as illustrated by the following reaction formula 4:

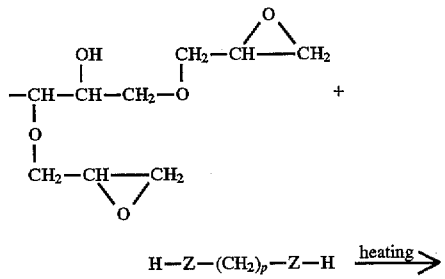

(4)

-continued

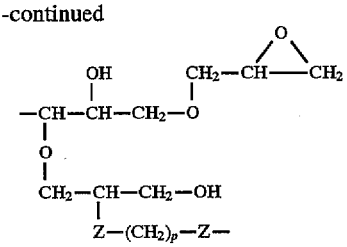

The resins represented by the formula [6] can be easily obtained by, for example, a synthesis process shown by the following reaction formula 5:

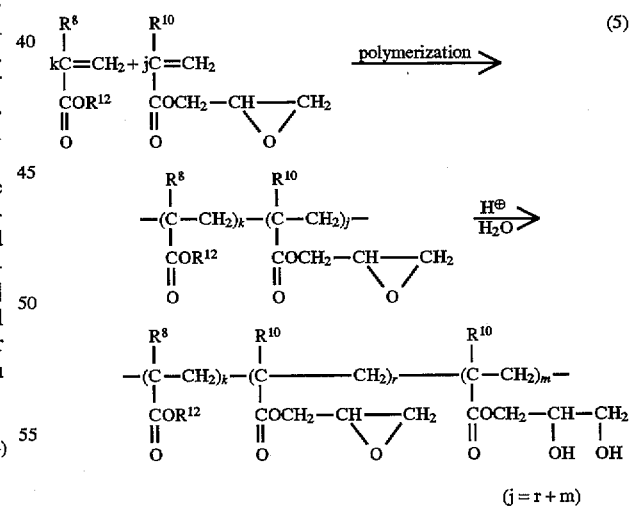

(5)

(j = r + m)

The synthesis of a resin of the formula [6] comprises dissolving at least two monomers (at least one of which has a glycidyl group in the molecule) of an appropriate ratio in 1 to 10 times as much volume of a suitable solvent (such as toluene, 1,4-dioxane, tetrahydrofuran, 1,3-dioxolan or the like) and reacting them in a nitrogen stream in the presence of a polymerization initiator [such as azobisisobutyronitrile, 2,2'-azobis(2,4-dimethylvaleronitrile), 2,2'-azobis(2-methyl methylpropionate), 2,2'-azobis(2-methylbutyronitrile), benzoyl peroxide, lauroyl peroxide or the like] of an amount of 0.1–20% by weight based on the monomers at 50°–150° C. for 1–20 hours, followed by the appropriate after-treatments according to a conventional method to give an objective copolymer (resin). If desired, the above copolymer may be dissolved in 1 to 20 times as much volume of a suitable solvent(such as acetone, 1,4-dioxane, toluene, tetrahydrofuran, methanol, ethanol, isoproanol or the like) and reacted in the presence of an acid (such as hydrochloric acid, sulfuric acid, p-toluenesulfonic acid, oxalic acid or the like) in an amount of 0.1–25% by weight based on the weight of the copolymer at 20°–150° C. for 1–20 hours, followed by the suitable after-treatments in a known way to give a resin having two or more hydroxyl groups in the molecule.

Examples of the compounds having one or more glycidyl groups in the molecule usable in the present invention (which compounds may hereinafter be referred to as resin according to the present invention) include poly(methyl methacrylate/glycidyl methacrylate), poly(methyl methacrylate/glycidyl methacrylate/2,3-dihydroxypropyl methacrylate), poly(cyclohexyl methacrylate/glycidyl methacrylate), poly(n-butyl methacrylate/glycidyl methacrylate), poly(tert-butyl methacrylate/glycidyl methacrylate), poly(methyl methacrylate/glycidyl methacrylate/tert-butyl methacrylate), poly(methyl methacrylate/glycidyl methacrylate/2-hydroxyethyl methacrylate), poly(cyclohexyl methacrylate/glycidyl methacrylate/2,3-dihydroxypropyl methacrylate), poly(methyl acrylate/glycidyl methacrylate), poly(methyl acrylate/glycidyl methacrylate), poly(methyl methacrylate/glycidyl methacrylate/norbornyl methacrylate), poly(methyl methacrylate/glycidyl methacrylate/adamantyl methacrylate), poly(methylmethacrylate/glycidyl methacrylate/9-anthracenemethyl methacrylate), poly(ethyl acrylate/glycidyl methacrylate), poly(methyl methacrylate/glycidyl methacrylate/n-butyl methacrylate), poly(2-hydroxyethyl methacrylate/glycidyl methacrylate), poly (methyl methacrylate/glycidyl acrylate), and poly(vinyl alcohol/glycidyl methacrylate/methyl methacrylate). Of these resins, poly(methyl methacrylate/glycidyl methacrylate/9-anthracenemethyl methacrylate) is especially preferred because of relatively high absorption of light at around 250 nm.

The solvent used in the preparation of the deep ultraviolet absorbent of the present invention may be any of those capable of dissolving both of the crosslinking agents according to the present invention and the compounds having one or more glycidyl groups in the molecule. Exemplary of such solvents are diethylene glycol dimethyl ether, ethylene glycol monomethyl ether acetate, ethylene glycol monoethylether acetate, propylene glycol monomethyl ether acetate, propylene glycol monoethyl ether acetate, methyl lactate, ethyl lactate, methyl pyruvate, ethyl pyruvate, methyl 3-methoxypropionate, ethyl 3-methoxypropionate, 2-heptanone, N-metylpyrrolidone, cyclohexanone, tetrahydrofurfuryl alcohol, tetrahydrofuran, 1,4-dioxane, 1,2-dimethoxyethane, butyl acetate and methyl ethyl ketone.

For forming a pattern by using the deep ultraviolet absorbent according to the present invention, the following process is presented as a typical case.

First, the deep ultraviolet absorbent of this invention is coated as an undercoat on a highly reflective substrate made of aluminum, polysilicon, aluminum-silicon or the like to a thickness of about 50–500 nm and heated in an oven at 150°–230° C. for 5–30 minutes or on a hot plate at 150°–230° C. for 1–2 minutes to form a deep ultraviolet absorbent film. On this deep ultraviolet absorbent film is coated a chemically amplified resist material (which may be either positive type or negative type) to a thickness of about 0.5–2 μm, followed by baking in an oven at 70°–130° C. for 10–30 minutes or on a hot plate at 70°–130° C. for 1–2 minutes. Then the resist film is covered with a mask for forming the desired pattern and exposed to deep ultraviolet light with a wavelength of 300 nm or less at an exposure of about 1–100 mJ/cm$^2$, followed by baking on a hot plate at 70°–150° C., for 1–2 minutes.

Then the film is developed by a conventional method such as dipping, puddling or spraying method using an appropriate developing solution such as a 0.1–5% tetramethylammonium hydroxide (TMAH) solution for about 0.5–3 minutes to form the desired pattern on the substrate.

The mixing ratio (by weight) of the compound(s) having one or more glycidyl groups in the molecule (total weight in case two or more compounds are used) to the crosslinking agent(s) of this invention (total weight in case two or more crosslinking agents are used) in the deep ultraviolet absorbent according to the present invention is 1 to 0.1–1, preferably 0.15–0.75. The amount of the solvent in the deep ultraviolet absorbent of the present invention is not specified but can be optionally selected as far as no impediment is caused when the deep ultraviolet absorbent obtained by dissolving a compound having one or more glycidyl groups in the molecule and a crosslinking agent of this invention is coated on the substrate, but usually the ratio by weight of the solvent(s) (total weight in case of using two or more solvents) to the compound(s) having one or more glycidyl groups (total weight in case of using two or more compounds) is 1–50:1, preferably 10–25:1.

The resist material employed in pattern formation using the deep ultraviolet absorbent of this invention for undercoating may be either a chemically amplified positive resist material or a chemically amplified negative resist material.

As the developing solution used in the pattern forming process using the deep ultraviolet absorbent of this invention for undercoating, there is employed an alkaline developing solution having an appropriate concentration for causing dissolution of the exposed portion while scarcely inducing dissolution of the non-exposed portion, such concentration being usually selected from the range of 0.01–20% depending on the solubility of the resin component of the resist material in the alkaline developing solution in case of using a positive type resist material. The alkaline solution used for such developing solution is, for instance, a solution containing an organic amine such as TMAH, choline, triethanolamine, etc., and an inorganic alkali such as NaOH, KOH, etc.

The deep ultraviolet absorbent according to the present invention is principally composed of a compound having one or more glycidyl groups in the molecule, a crosslinking agent of the formula [1] and a solvent, but if necessary it may also contain one or more of the deep ultraviolet absorbing substances [such as 9-anthracenemethanol, 9-(2-methoxyethoxy)-methylanthracene, 9-(2-ethoxyethoxy) methylanthracene, 9-anthracenemethyl acetate, 9-anthracenemethyl propionate, di(9-anthracenemethyl) malonate, di(9-anthracenemethyl)terephthalate, 1,2,10-triacetoxyanthracene, 1,5,9-triacetoxyanthracene, 2,6,9-triacetoxyanthracene, 1,5,9-tribenzoyloxyanthracene, 1,2,10-tribenzoyloxyanthracene, 2,6,9-tribenzoyloxyanthracene, etc.] and the commercially available surfactants (such as various types of nonionic and fluorine-containing nonionic surfactants) for improving the coating properties.

When the deep ultraviolet absorbent of this invention is spin coated on a semiconductor substrate and heated to 150° C. or above, a crosslinking reaction occurs between the compound having one or more glycidyl groups in the molecule and the crosslinking agent of this invention as schematically shown by the following reaction formula 6 to form an anti-reflective film with excellent heat resistance.

The crosslinking agent and the resin having one or more glycidyl (epoxy) groups in the molecule usable in the present invention are soluble in acetone or a solvent used for forming a resist solution (e.g. propylene glycol monomethyl ether acetate, etc.), but once an antireflection coating is formed from these compounds by the crosslinking reaction shown by the reaction formula 6, the antireflection coating is not soluble in the solvents mentioned above.

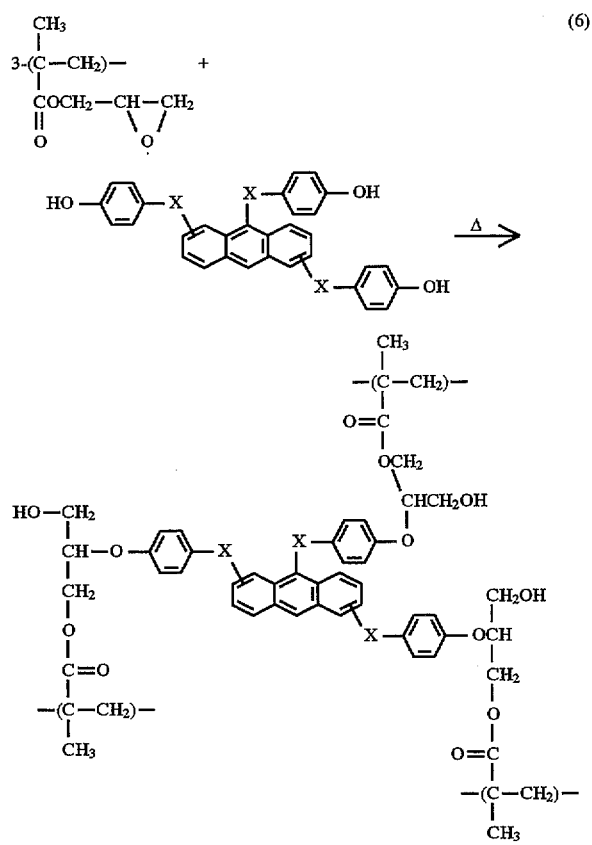

The heating conditions for the above reaction are not specified; there can be employed any conditions that can induce a crosslinking reaction between the compound having one or more glycidyl groups in the molecule and the crosslinking agent of the formula [1].

Then a resist material suited for KrF excimer laser is coated on the surface of said anti-reflective film and baked to form a resist film. When deep ultraviolet light such as KrF excimer laser light is applied to this film, the light which has passed the resist film is absorbed due to the anthracene rings contained in the anti-reflective film to prevent reflection from the semiconductor substrate. It is thus possible to perfectly eliminate the influence of intra-film multiple reflection which has been a serious problem in this field of art, and there is caused no dimensional variation due to the influence of reflection even in resist pattern formation on a semiconductor substrate which has a level difference due to a difference in film thickness.

Further, since this anti-reflective film is not dissolved by the resist solvent, it does not intermix with the resist at the interface therebetween and gives no influence to pattern resolution.

Compounds similar to the anthracene derivative of the formula [1] used as the crosslinking agent are disclosed in DE-OS 2,257,442 wherein three groups represented by the formula [2] wherein X=—OCO— are introduced into the 1, 8 and 9 positions of the anthracene ring at the same time, for example, 1,8,9-tris(4-hydroxybenzoyloxy)anthracene, 1,8,9-tris(2-hydroxybenzoyloxy)anthracene, etc. But when these compounds are mixed with a resin having one or more glycidyl groups in the molecule and heated, the crosslinking reaction hardly proceeds due to steric hindrance and/or a strong intramolecular hydrogen bond, resulting in maintaining the solubility in acetone and a solvent for resist solutions. Therefore, when such compounds are used for making the antireflective coating, the desired antireflective coating cannot be obtained at all due to intermixture with the resist at the interface portion.

The present invention is further illustrated below by showing the Synthesis Examples, Examples and Comparative Examples, but it is to be understood that the present invention is not subject to any restrictions by these Examples.

SYNTHESIS EXAMPLE 1

Synthesis of 2,6,9-tris(4-hydroxybenzoyloxy) anthracene (1) A suspension of p-hydroxybenzoic acid (200 g, 1.2 mole), benzyl chloride (190 g, 1.5 mole) and potassium carbonate (165 g, 1.2 mole) in acetone (1200 ml) was reacted with stirring for 12 hours under reflux. After cooling, the precipitate was filtered off, and the filtrate was concentrated until 400 ml. $H_2O$ (1 l) was added with stirring to the residue and the mixture was allowed to stand. The organic layer separated was concentrated. The residue was added to a solution of NaOH (60 g, 1.5 mole) in $H_2O$ (1 l) and ethanol (500 ml), and stirred for 4 hours and dissolved. Then conc. hydrochloric acid (200 ml) was added to make pH 1. The precipitate was filtered, washed with $H_2O$ and with ethanol, and dried to give 195 g of 4-benzyloxybenzoic acid as white crystals having a m.p. of 191.2°–192.6° C.

$^1$HNMR δ ppm ($CDCl_3$/DMSO-$d_6$): 5.10 (2H, s, ArC$\underline{H_2}$O—), 6.92 (2H, d, J=8 Hz, Ar 3-H, 5-H), 7.13–7.51 (5H, m, ArH), 7.86 (2H, d, J=8 Hz, Ar 2-H, 6-H), 8.65 (1H, bs, O$\underline{H}$).

IR (KBr-disk) ν $cm^{-1}$: 1675 (COOH).

(2) To a suspension of 4-benzyloxybenzoic acid (16 g, 70 mmole) obtained in above (1) in methylene chloride (50 ml), thionyl chloride (20.6 g, 173 mmole) and N,N-dimethylformamide (2 drops) were added, and reacted with stirring at 45°–50° C. for 1 hour. After standing at room temperature overnight, the solvent was removed to give 17.3 g of 4-benzyloxybenzoyl chloride as white crystals.

(3) To a solution of 2,6-dihydroxy-9-anthrone (5 g, 22 mmole) in pyridine (110 ml) and triethylamine (8.8 g), 4-benzyloxybenzoyl chloride (17.0 g, 69 mmole) obtained in above (2) was added in a small portion. The mixture was reacted with stirring at 100° C. for 5 hours and cooled to room temperature. The reaction mixture was poured into 1N hydrochloric acid (600 ml), extracted with methylene chloride (250 ml). The methylene chloride layer was washed with 1N hydrochloric acid (600 ml×1) and then saturated aqueous NaCl solution (500 ml×3), and dried over anhydrous MgSO$_4$. After removing the drying agent and the solvent, the residual oil (26 g) was crystallized from a mixture of n-hexane and tetrahydrofuran [1/2(v/v)] to afford 7.45 g of 2,6,9-tris(4-benzyloxybenzoyloxy)anthracene as yellow crystals having a melting point of 219°–221° C.

$^1$HNMR δ ppm (CDCl$_3$): 5.15, 5.17 and 5.20 (each 2H, each s, each ArC$\underline{H}_2$O—), 7.03–8.40 (34H, m, ArH).

IR (KBr-disk) ν cm$^{-1}$: 1728 (COO—).

(4) A solution of 2,6,9-tris(4-benzyloxybenzoyloxy) anthracene (6.2 g, 7.3 mmole) obtained in above (3) in tetrahydrofuran (250 ml) was hydrogenated for 6 hours at room temperature at 1 atm. in the presence of 5% palladium on carbon (11.5 g). After reaction, the catalyst was filtered off. The filtrate was concentrated and residual yellow solid (4.2 g) was recrystallized from the mixture of n-hexane and tetrahydrofuran [1/5(v/v)] to give 3.0 g of 2,6,9-tris(4-hydroxybenzoyloxy)anthracene as pale yellow crystals having a melting point of 238° C. (decomp.).

$^1$HNMR δ ppm (DMSO-d$_6$): 6.90–7.04 (6H, m, (Ar 3'-H, 5'-H)×3), 7.50–8.29 (12H, m, (Ar 2'-H, 6'-H)×3) and Anthracene ring 1-H, 3-H, 4-H, 5-H, 7-H, 8-H), 8.67 (1H, s, Anthracene ring 10-H), 10.60 (3H, bs, O$\underline{H}$×3).

IR (KBr-disk) ν cm$^{-1}$: 3392 (OH), 1699 (COO—).

SYNTHESIS EXAMPLE 2

Synthesis of 2,6-bis(4-hydroxybenzoyloxy) anthracene (1) To a suspension of 2,6-dihydroxyanthraquinone (3 g, 12.5 mmole) and anhydrous potassium carbonate (23 g) in acetone (400 ml), dimethyl sulfate (20 g, 158 mmole) was added at room temperature, and the mixture was reacted with stirring for 6 hours under reflux. After standing at room temperature overnight, the reaction mixture was poured into cold H$_2$O (850 ml), and the precipitate was filtered and dried. The resultant crude dark brown solid (3.1 g) was recrystallized from benzene to give 2.7 g of 2,6-dimethoxyanthraquinone as yellow-brown crystals.

$^1$HNMR δ ppm (DMSO-d$_6$): 3.97 (6H, s, C$\underline{H}_3$O×2), 7.43 (2H, d, J=8 Hz, Anthraquinone ring 3-H, 7-H), 7.61 (2H, s, Anthraquinone ring 1-H, 5-H), 8.17 (2H, d, J=8 Hz, Anthraquinone ring 4-H, 8-H).

IR (KBr-disk) ν cm$^{-1}$: 1668 (C=O).

(2) To a suspension of 2,6-dimethoxy-9,10-anthraquinone (2.7 g, 10 mmole) obtained in above (1) in 25% aqueous ammonia (92 ml), zinc powder (10.2 g, 156 mmole) and cupric sulfate 5 hydrate (130 mg) were added. The mixture was stirred for 7 hours at 70° C. and cooled to room temperature. The reaction mixture was neutralized with 1N sulfuric acid (40 ml), and methylene chloride and H$_2$O were added with stirring. The precipitate was filtered off and the filtrate was separated. The organic layer separated was washed with H$_2$O, evaporated and residual crude solid (2.2 g) was recrystallized from methanol to give 1.3 g of 2,6-dimethoxyanthracene as yellow-brown crystals.

$^1$HNMR δ ppm (CDCl$_3$): 3.80 (6H, s, C$\underline{H}_3$O×2), 6.51–8.20 (8H, m, ArH).

IR (KBr-disk) ν cm$^{-1}$: 1613, 1577.

(3) To a suspension of 2,6-dimethoxyanthracene (1.22 g, 5.1 mmole) obtained in above (2) in methylene chloride (30 ml), a solution of boron tribromide (3.2 g, 12.8 mmole) in methylene chloride (10 ml) was added dropwise at −60° C. The temperature of the resulting mixture was raised slowly to room temperature, and allowed to stand at room temperature overnight. The reaction mixture was poured into cold H$_2$O (200 ml). The precipitate was filtered, washed with H$_2$O and dried to afford 0.85 g of 2,6-dihydroxyanthracene as a crude yellow-brown solid.

$^1$HNMR δ ppm (DMSO-d$_6$): 6.07–8.15 (8H, m, ArH), 9.65 (2H, bs, O$\underline{H}$×2).

(4) To a solution of 2,6-dihydroxyanthracene (0.82 g, 3.9 mmole) obtained in above (3) in pyridine (15 ml), 4-benzyloxybenzoyl chloride (2.12 g, 8.58 mmole) obtained in Synthesis Example 1, (1) was added. Then triethylamine (1 g) was added dropwise at 20° C., and the mixture was reacted with stirring for 8 hours at 90°–95° C. The reaction mixture was cooled, poured into dilute HCl (400 ml), and extracted with methylene chloride. The organic layer separated was washed with H$_2$O and evaporated. The crude oily residue was chromatographed on silica gel (Wakogel C-200, a trade name, mfd. by Wako Pure Chemical Industries, Ltd.) with n-hexane/methylene chloride (7/1→2/1→1/1→1/2) as eluent to give 0.56 g of 2,6-bis(4-benzyloxybenzoyloxy)anthracene as a yellow powder.

$^1$HNMR δ ppm (CDCl$_3$): 5.09 and 5.17 (each 2H, each s, each ArC$\underline{H}_2$O—), 6.82–8.66 (26H, m, ArH).

IR (KBr-disk) ν cm$^{-1}$: 1732 (COO—).

(5) Using 2,6-bis(4-benzyloxybenzoyloxy)anthracene (0.56 g, 0.88 mmole) obtain in above (4), the catalytic reduction was carried out in the same manner as described in Synthesis Example 1, (4) to afford 0.36 g of 2,6-bis(4-hydroxybenzoyloxy)anthracene as pale yellow crystals having a melting point of 324° C. (decomp.).

$^1$HNMR δ ppm (DMSO-d$_6$): 6.63–8.97 (16H, m, ArH), 10.48 (2H, bs, O$\underline{H}$×2).

IR (KBr-disk) ν cm$^{-1}$: 3405 (OH), 1701 (COO—).

SYNTHESIS EXAMPLE 3

Synthesis of 1,5,9-tris(4-hydroxybenzoyloxy) anthracene (1) To a suspension of 1,5-dihydroxyanthraquinone (10 g, 41.6 mmole) and stannous chloride (45 g, 237 mmole) in glacial acetic acid (150 ml), conc. hydrochloric acid (90 ml) was added at 16°–20° C. The mixture was stirred for 4 hours under reflux. After standing at room temperature overnight, the reaction mixture was cooled to 5° C. The precipitate was filtered, washed with H$_2$O and dried to afford 8.0 g of 1,5-dihydroxyanthrone as dark brown needles having a m.p. of 231°–233° C.

$^1$HNMR δ ppm (DMSO-d$_6$): 4.20 (2H, s, C$\underline{H}_2$), 6.87 (1H, d, J=8 Hz, Anthracene ring 6-H), 7.09 (1H, d, J=8 Hz, Anthracene ring 2-H), 7.19 (1H, d, J=8 Hz, Anthracene ring 4-H), 7.35 (1H, t, J=8 Hz, Anthracene ring 7-H), 7.57 (1H, t, J=8 Hz, Anthracene ring 3-H), 7.69 (1H, d, J=8 Hz, Anthracene ring 8-H), 10.23 (1H, bs, 5-O$\underline{H}$), 12.97 (1H, s, 1-O$\underline{H}$).

IR (KBr-disk) ν cm$^{-1}$: 3338 (OH), 1633 (C=O).

(2) To a solution of 1,5-dihydroxy-9-anthrone (2.3 g, 10 mmole) obtained in above (1) in pyridine (45 ml) and triethylamine (3.6 g), 4-benzyloxybenzoyl chloride (8 g) obtained in Synthesis Example 1, (2) was added in a small portion, continued to stir for 5 hours at 90° C., and allowed to stand at room temperature overnight. The reaction mixture was poured into 1N hydrochloric acid (300 ml), extracted with methylene chloride. The organic layer separated was washed with H$_2$O, dried over anhydrous MgSO$_4$ and evaporated. The residue was chromatographed on silica gel (Wakogel C-200, a trade name, mfd. by Wako Pure Chemical Industries, Ltd.) with n-hexane/ methylene chloride (1/1→1/3) as eluent to afford 2.0 g of 1,5,9-tris(4-benzyloxybenzoyloxy)anthracene as yellow crystals having a m.p. of 240°–242° C.

$^1$HNMR δ ppm (CDCl$_3$): 5.00, 5.03 and 5.23 (each 2H, each s, each ArC$\underline{H}_2$O—), 6.67–8.54 (34H, m, ArH).

IR (KBr-disk) ν cm$^{-1}$: 1735 (COO—).

(3) Using 1,5,9-tris(4-benzyloxybenzoyloxy)anthracene (1 g, 1.14 mmole) obtained in above (2), the catalytic reduction was carried out in the same manner as described in Synthesis Example 1, (4). The crude solid (0.7 g) was recrystallized from a mixture of tetrahydrofuran and n-hexane to give 0.5 g of 1,5,9-tris(4-hydroxybenzoyloxy)anthracene as pale yellow crystals having a m.p. of 326° C.

$^1$HNMR δ ppm (DMSO-d$_6$): 6.55–7.06 (6H, m, Phenyl ring (3-H, 5-H)×3), 7.32–8.23 (12H, m, Anthracene ring 2-H, 3-H, 4-H, 6-H, 7-H, 8-H and Phenyl ring (2-H, 6-H) ×3), 8.65 (1H, s, Anthracene ring 10-H), 10.41 (3H, bs, O $\underline{H}$×3).

IR (KBr-disk) ν cm$^{-1}$: 3408 (OH), 1702 (COO—).

SYNTHESIS EXAMPLE 4

Synthesis of 1,2,10-tris(4-hydrobenzoyloxy) anthracene (1) Using 1,2-dihydroxy-10-anthrone (2.26 g) and 4-benzyloxybenzoyl chloride (8 g) obtained in Synthesis Example 1, (2), the reaction was carried out in the same manner as described in Synthesis Example 1, (3). The crude solid (3.5 g) was chromatographed on silica gel (Wakogel C-200, a trade name, mfd. by Wako Pure Chemical Industries, Ltd.) with n-hexane/methylene chloride [4/1→2/1→1/1 (v/v)] as eluent to give 1.6 g of 1,2,10-tris(4-benzyloxybenzoyloxy)anthracene as yellow crystals.

$^1$HNMR δ ppm (CDCl$_3$): 5.09, 5.16 and 5.23 (each 2H, each s, each ArC$\underline{H}_2$O—), 6.91–8.44 (34H, m, ArH).

IR (KBr-disk) ν cm$^{-1}$: 1740 (COO—).

(2) Using 1,2,10-tris(4-benzyloxybenzoyloxy)anthracene (1.54 g, 1.8 mmole) obtained in above (1), the catalytic reduction was carried out in the same manner as described in Synthesis Example 1, (4). The crude solid (0.92 g) was recrystallized from a mixture of tetrahydrofuran and n-hexane to give 0.5 g of 1,2,10-tris(4-hydroxybenzoyloxy)anthracene as pale yellow crystals.

$^1$HNMR δ ppm (DMSO-d$_6$): 6.79–7.08 (6H, m, Phenyl ring (3-H, 5-H)×3), 7.49–8.29 (12H, m, Anthracene ring 3-H, 4-H, 5-H, 6-H, 7-H, 8-H and Phenyl ring (2-H, 6-H) ×3), 8.59 (1H, s, Anthracene ring 9-H), 10.59 (3H, bs, OH×3).

IR (KBr-disk) ν cm$^{-1}$: 3413 (OH), 1706 (COO—).

SYNTHESIS EXAMPLE 5

Synthesis of 2,6,9-tris(4-hydroxy-3-methoxybenzoyloxy)anthracene (1) To a suspension of 4-hydroxy-3-methoxybenzoic acid (25 g, 0.15 mole) in ethanol (150 ml), 2N NaOH aq. (74.3 g, 0.15 mole) and benzyl chloride (56.5 g, 0.45 mole) were added, continued to stir for 1 hour under reflux. Then, 5N NaOH aq. (150 ml) was added dropwise with stirring under reflux, and continued to stir for 1 hour under reflux. After reaction, the solvent was removed, and H$_2$O was added to the residue and acidified with conc. hydrochloric acid to make pH 1. The precipitate was filtered, washed with H$_2$O and dried to give 22.1 g of 4-benzyloxy-3-methoxybenzoic acid as pale yellow crystals having a m.p. of 171°–172.5° C.

$^1$HNMR δ ppm (DMSO-d$_6$): 3.81 (3H, s, C$\underline{H}_3$O—), 5.16 (2H, s, ArC$\underline{H}_2$O—), 7.13 (1H, d, J=8 Hz, Ar 5-H), 7.33–7.44 (5H, m, ArH), 7.47 (1H, d, J=2 Hz, Ar 2-H), 7.54 (1H, dd, J=2 Hz and 8 Hz, Ar 6-H).

IR (KBr-disk) ν cm$^{-1}$: 1676 (COOH).

(2) A suspension of 4-benzyloxy-3-methoxybenzoic acid (22.3 g, 86.3 mmole) obtained in above (1) in thionyl chloride (30.8 g, 0.26 mole) was heated slowly, and reacted with stirring for 2 hours at 60°–65° C. The reaction mixture was concentrated to afford 23.4 g of 4-benzyloxy-3-methoxybenzoyl chloride as pale yellow leaflets having a m.p. of 63°–65° C.

(3) Using 4-benzyloxy-3-methoxybenzoyl chloride (10.1 g, 36.4 mmole) obtained in above (2) and 2,6-dihydroxy-9-anthrone (2.2 g, 11 mmole), the reaction was carried out in the same manner as described in Synthesis Example 1, (3) to afford 7.8 g of 2,6,9-tris(4-benzyloxy-3-methoxybenzoyloxy)anthracene as pale yellow crystals having a m.p. of 186°–189° C.

$^1$HNMR δ ppm (CDCl$_3$): 3.96, 3.99 and 4.00 (each 3H, each s, each C$\underline{H}_3$O—), 5.25, 5.27 and 5.29 (each 2H, each s, each ArC$\underline{H}_2$O—), 6.93–8.09 (30H, m, ArH), 8.39 (1H, Anthracene ring 10-H).

IR (KBr-disk) ν cm$^{-1}$: 1736 (COO—).

(4) Using 2,6,9-tris(4-benzyloxy-3-methoxybenzoyloxy) anthracene (2.4 g, 2.52 mmole) obtained in above (3), the catalytic reduction was carried out in the same manner as described in Synthesis Example 1, (4). The crude solid (1.6 g) was recrystallized from a mixture of tetrahydrofuran and n-hexane to give 0.9 g of 2,6,9-tris (4-hydroxy-3-methoxybenzoyloxy)anthracene as pale yellow crystals having a m.p. of 206° C. (decomp.).

$^1$HNMR δ ppm (DMSO-d$_6$): 3.94, 3.97 and 3.98 (each 3H, each s, each CH$_3$O—), 7.01–8.39 (15H, m, ArH), 8.78 (1H, s, Anthracene ring 10-H), 10.33 (3H, bs, OH×3).

IR (KBr-disk) ν cm$^{-1}$: 3374 (OH), 1728 (COO—).

SYNTHESIS EXAMPLE 6

Synthesis of 1,2,10-tris(4-hydroxybenzenesulfonyloxy)anthracene (1) To a suspension of sodium p-hydroxybenzenesulfonate (40 g, 0.17 mole) in a solution of NaOH (9.61 g, 0.24 mole) and H$_2$O (55 ml), a solution of benzyl chloride (27.6 g, 0.22 mole) in ethanol (35 ml) was added dropwise, and continued to stir for 5 hours under reflux. After standing at room temperature overnight, the precipitate was filtered, washed with H$_2$O and dried to afford 35.2 g of sodium p-benzyloxybenzenesulfonate as white crystals.

(2) Sodium p-benzyloxybenzenesulfonate (30 g, 105 mmole) obtained in above (1), was added in a small portion to thionyl chloride (46 g, 387 mole) at 45° C. or below. Then N,N-dimethylformamide (0.5 g) was added, and the mixture was reacted with stirring at 50°–60° C. for 3.5 hours, then for 4 hours under reflux. After standing at room temperature overnight, the solvent was removed to give 29.1 g of p-benzyl oxybenzenesulfonyl chloride as white crystals having a m.p. of 95°–97.5° C.

$^1$HNMR δ ppm (DMSO-d$_6$): 5.10 (2H, s, ArC$\underline{H}_2$O—), 6.95 (2H, d, J=8.8 Hz, Ar 2-H, 6-H), 7.29–7.43 (5H, m, ArH), 7.54 (2H, d, J=8.8 Hz, Ar 3-H, 5-H).

IR (KBr-disk) ν cm$^{-1}$: 1370, 1190, 1170

(3) To a suspension of 1,2-dihydroxy-10-anthrone (4 g, 17.7 mmole) and triethylamine (6.2 g, 61 mmole) in methylene chloride (100 ml), 4-benzyloxybenzenesulfonyl chloride (15.8 g, 58 mmole) obtained in above (2) was added in a small portion at 5°–10° C., stirred at 18°–23° C. for 5 hours and allowed to stand at room temperature overnight. The reaction mixture was extracted with methylene chloride (50 ml). The methylene chloride layer was washed with 0.1N HCl (70 ml×l), saturated NaHCO$_3$ aq. (70 ml×l), then H$_2$O (70 ml×l), and dried over anhydrous MgSO$_4$. After removing the drying agent and solvent, the residual oil (18 g) was chromatographed on silica gel (Wakogel C-200, a trade name, mfd. by Wakogel Pure Chemical Industries, Ltd.) with n-hexane/methylene chloride [4/1→3/1→2/1 (v/v)] as eluent to give 5.75 g of 1,2,10-tris(4-benzyloxybenzenesulfonyloxy)anthracene as yellow crystals.

$^1$HNMR δ ppm (CDCl$_3$): 5.07 (2H, s, ArCH$_2$O—), 5.18 (4H, s, ArCH$_2$O—×2), 6.82–8.05 (33H, m, ArH except for Aromatic 10-H), 8.49 (1H, s, ArH 10-H).

IR (KBr-disk) ν cm$^{-1}$: 1370, 1195, 1170.

(4) A solution of 1,2,10-tris(4-benzyloxybenzenesulfonyloxy)anthracene (3.8 g, 4 mmole) obtained in above (3) in tetrahydrofuran (80 ml) was hydrogenated for 5 hours at room temperature at 1 atm. in the presence of 5% palladium on carbon (10 g). After reduction, the catalyst was filtered off. The filtrate was evaporated under reduced pressure, and the residual orange oil (1.7 g) was chromatographed on silica gel (Wakogel C-200) with methylene chloride/methanol [20/1(v/v)] as eluent to give 0.85 g of 1,2,10-tris(4-hydroxybenzenesulfonyloxy)anthracene as yellow crystals.

$^1$HNMR δ ppm (DMSO-d$_6$): 6.89–8.14 (18H, m, ArH except for Azomatic 10-H), 8.44 (1H, s, Ar 10-H), 9.74 (1H, bs, OH).

IR (KBr-disk) ν cm$^{-1}$: 3440 (OH), 1370, 1190, 1167.

SYNTHESIS EXAMPLE 7

Synthesis of 1,5,9-tris(4-hydroxybenzenesulfonyloxy)anthracene (1) To a solution of 1,5-dihydroxy-9-anthrone (1.5 g, 6.6 mmole) obtained in Synthesis Example 3, (1) in methylene chloride (40 ml), triethylamine (2.33 g, 23 mmole) was added at 10° C. or below. Then 4-benzyloxybenzenesulfonyl chloride (5.9 g, 20.8 mmole) obtained in Synthesis Example 6, (2) was added in a small portion at 8°–12° C. to the mixture and the reaction was carried out in the same manner as described in Synthesis Example 6, (3). The resultant crude oil (5.2 g) was chromatographed on silica gel (Wakogel C-200, a trade name, mfd. by Wako Pure Chemical Industries, Ltd.) with n-hexane/methylene chloride [1/1→4/1→1/1→1/2 (v/v)] as eluent to give 1.8 g of 1,5,9-tris(4-benzyloxybenzenesulfonyloxy)anthracene as orange yellow crystals.

$^1$HNMR δ ppm (CDCl$_3$): 4.85, 5.02 and 5.11 (each 2H, each s, each ArCH$_2$O—), 6.69, 6.88 and 6.95 (each 2H, each d, each J=8.6 Hz, each Phenyl ring (3-H, 5-H)×3), 7.02–7.87 (27H, m, Phenyl ring (2-H, 6-H)×3, ArCH$_2$H×3 and Anthracene ring 2-H, 3-H, 4-H, 6-H, 7-H, 8-H), 8.38 (1H, s, Anthracene ring 10-H).

IR (KBr-disk) ν cm$^{-1}$: 1378, 1192, 1170.

(2) Using 1,5,9-tris(4-benzyloxy benzenesulfonyoxy) anthracene (0.5 g, 0.5 mmole) obtained in above (1), the catalytic reduction was carried out in the same manner as described in Synthesis Example 6, (4) to give 0.18 g of 1,5,9-tris(4-hydroxybenzenesulfonyloxy)anthracene as residual pale yellow crystals.

$^1$HNMR δ ppm (Acetone-d$_6$): 6.55, 6.72 and 6.77 (each 2H, each d, each J=8.6 Hz, each Phenyl ring (3-H, 5-H)×3), 7.09–7.89 (12H, m, Anthracene ring 2-H, 3-H, 4-H, 6-H, 7-H, 8-H and Phenyl ring (2-H, 6-H)×3), 8.28 (1H, s, Anthracene ring 10-H), 9.62 (3H, s, OH×3).

IR (KBr-disk) ν cm$^{-1}$: 3418 (OH), 1367, 1192, 1167.

SYNTHESIS EXAMPLE 8

Synthesis of 2,6,9-tris(4-hydrobenzenesulfonyloxy)anthracene (1) To a solution of 2,6-dihydroxy-9-anthrone (1 g, 4.4 mmole) in pyridine (20 ml) and methylene chloride (27 ml), triethylamine (1.56 g) was added at 10° C. or below. Then 4-benzyloxybenzenesulfonyl chloride (3.94 g, 13.9 mmole) obtained in Synthesis Example 6, (2) was added in a small portion at 8°–12° C. to the mixture and the reaction was carried out in the same manner as described in Synthesis Example 6, (3). The crude solid (3.3 g) was chromatographed on silica gel (Wakogel C-200) with n-hexane/methylene chloride [8/1→2/1→1/1 (v/v)] as eluent and then recrystallized from n-hexane/ethyl acetate to give 1.2 g of 2,6,9-tris(4-benzyloxybenzenesulfonyloxy)anthracene as pale yellow crystals having a m.p. of 163.5°–165.5° C.

$^1$HNMR δ ppm (CDCl$_3$): 5.07, 5.11 and 5.18 (each 2H, each s, each ArCH$_2$O—), 6.99–7.09 (7H, m, Phenyl ring (3-H, 5-H)×3 and Anthracene ring 7-H), 7.17 (1H, dd, J=2.2 Hz and 9.5 Hz, Anthracene ring 3-H), 7.28–7.46 (15H, m, ArH×3), 7.49 (1H, d, J=2.2 Hz, Anthracene ring 1-H), 7.61 (1H, d, J=2.2 Hz, Anthracene ring 5H), 7.75–7.84 (6H, m, Phenyl ring (2-H, 6H)×3), 7.87 (1H, d, J=9.5 Hz Anthracene ring 8H), 7.96 (1H, d, J=9.5 Hz, Anthracene ring 4H), 8.24 (1H, s, Anthracene ring 10-H).

IR (KBr-disk) ν cm$^{-1}$: 1371, 1192, 1170.

(2) Using 2,6,9-tris(4-benzyloxybenzenesulfonyloxy)anthracene (1.05 g, 1.1 mmole) obtained in above (1), the catalytic reduction was carried out in the same manner as described in Synthesis Example 6, (4). The residue was crystallized from methylene chloride to give 0.4 g of 2,6,9-tris(4-hydroxybenzenesulfonyloxy)anthracene as pale yellow crystals having a m.p. of 192°–194.5° C. (Decomp.).

$^1$HNMR δ ppm (CDCl$_3$): 6.91–7.01 (6H, m, Phenyl ring (3-H, 5-H)×3), 7.20–7.27 (2H, m, Anthracene ring 3-H, 7-H), 7.39 (1H, d, J=1.8 Hz, Anthracene ring 1-H), 7.63–7.74 (6H, m, Phenyl ring (2-H, 6-H)×3), 7.79 (1H, d, J=9.5 Hz, Anthracene ring 5-H), 7.93 (1H, d, J=9.5 Hz Anthracene ring 8-H), 8.15 (1H, d, J=9.5 Hz, Anthracene ring 4-H), 8.66 (1H, s, Anthracene ring 10-H), 10.88, 10.91 and 11.05 (each 1H, each s, each OH).

IR (KBr-disk) ν cm$^{-1}$: 3401 (OH), 1363, 1188, 1167.

SYNTHESIS EXAMPLE 9

Synthesis of 2,6,9-tris(3,4-dihydroxybenzoyloxy)anthracene (1) To a suspension of 3,4-dihydroxybenzoic acid (25.4 g, 0.17 mole) in ethanol (250 ml), 5N NaOH aq. (270 ml) and benzyl chloride (102 g, 0.81 mole) were added, and the mixture was reacted with stirring for 6 hours under reflux. The reaction mixture was cooled to room temperature, allowed to stand at same temperature overnight and acidified with conc. hydrochloric acid (40 ml). The precipitate was filtered, washed with hot ethanol and dried under reduced pressure to give 38.2 g of 3,4-dibenzyloxybenzoic acid as pale yellow crystals having a m.p. of 184°–186° C.

$^1$HNMR δ ppm (DMSO-d$_6$): 3.38 (1H, bs, OH), 5.18 and 5.22 (each 2H, each s, each ArCHO—), 7.16 (1H, d, J=8.8 Hz, Ar 5-H), 7.30–7.57 (12H, m, ArH).

IR (KBr-disk) ν cm$^{-1}$: 1679 (C=O).

(2) A mixture of 3,4-dibenzyloxybenzoic acid (10 g, 30 mmole) obtained in above (1) and thionyl chloride (10.7 g, 90 mmole) was heated slowly, reacted with stirring for 1 hour at 85° C. and then evaporated in vacuo to give 10.3 g of 3,4-dibenzyloxy benzoyl chloride as white crystals having a melting point of 92.5°–94.5° C.

(3) Using 3,4-dibenzyloxybenzoyl chloride (5.2 g, 14.6 mmole) obtained in above (2) and 2,6-dihydroxy-9-anthrone (1 g, 4.4 mmole), the reaction was carried out in the same manner as described in Synthesis Example 1, (3). The crude solid (5.4 g) was recrystallized from methylene chloride/ethyl acetate [1/4 (v/v)] to afford 3.4 g of 2,6,9-tris(3,4-dibenzyloxybenzoyloxy)anthracene as yellow crystals having a m.p. of 189°–191° C.

$^1$HNMR δ ppm (CDCl$_3$): 5.20–5.31 (12H, m, ArCH$_2$O—×6), 7.14–8.05 (44H, m, ArH) 8.21 (1H, d, J=9.2 Hz, Anthracene ring 4-H), 8.58 (1H, s, Anthracene ring 10-H).

IR (KBr-disk) ν cm$^{-1}$: 1733 (COO—).

(4) Using 2,6,9-tris(3,4-dibenzyloxybenzoyloxy)anthracene (2 g, 1.7 mmole) obtained in above (3), the catalytic reduction was carried out in the same manner as described in Synthesis Example 1, (4). The crude solid (1.8 g) was recrystallized from tetrahydrofuran/n-hexane (5/7) to afford 2 g of 2,6,9-tris(3,4-dihydroxybenzoyloxy)anthracene as pale yellow crystals having a m.p. of 233° C. (Decomp.).

$^1$HNMR δ ppm (DMSO-d$_6$): 6.87–8.08 (14H, m, ArH), 8.27 (1H, d, J=9.2 Hz, Anthracene ring 4-H), 8.67 (1H, s, Anthracene ring 10-H), 9.77 (6H, bs, OH×6).

IR (KBr-disk) ν cm$^{-1}$: 3365 (OH), 1701 (COO—).

SYNTHESIS EXAMPLE 10

Synthesis of 1,2,10-tris(3-chloro-4-hydroxybenzoyloxy)anthracene (1) Using 3-chloro-4-hydroxybenzoic acid 1/2 hydrate (25 g, 0.14 mole) and benzyl chloride (52.3 g, 0.41 mole), the reaction was carried out in the same manner as described in Synthesis Example 1, (1) to give 20.4 g of 4-benzyloxy-3-chlorobenzoic acid as white crystals having a m.p. of 211°–213° C.

$^1$HNMR δ ppm (DMSO-d$_6$): 5.30 (2H, s, ArCH$_2$O—), 7.34 (1H, d, J=8.4 Hz, Ar 5-H), 7.37–7.49 (5H, m, ArH), 7.88 (1H, dd, J=1.8 Hz and 8.4 Hz, Ar 6-H), 7.93 (1H, d, J=1.8 Hz, Ar 2-H), 11.15 (1H, bs, COOH)

IR (KBr-disk) ν cm$^{-1}$: 1683 (COOH).

(2) Using 4-benzoxy-3-chlorobenzoic acid (2.0 g, 7.6 mmole) obtained in above (1), the reaction was carried out in the same manner as described in Synthesis Example 1, (2) to give 2.1 g of 4-benzyloxy-3-chlorobenzoylchloride as light brown crystals having a m.p. of 78°–80° C.

IR (KBr-disk) ν cm$^{-1}$: 1751 (C=O).

(3) Using 4-benzyloxy-3-chlorobenzoyl chloride (1.6 g, 5.7 mmole) obtained in above (2) and 1,2-dihydroxy-10-anthrone (0.4 g, 1.7 mmole), the reaction was carried out in the same manner as described in Synthesis Example 1, (3). The crude solid (1.1 g) was chromatographed on silica gel (Wakogel C-200, a trade name, mfd. by Wako Pure Chemical Industries, Ltd.) with n-hexane/methylene chloride [4/1→3/1→1/1 (v/v)] as eluent to give 0.65 g of 1,2,10-tris(4-benzyloxy-3-chlorobenzoyloxy)anthracene as pale yellow crystals having a m.p. of 106°–109° C.

$^1$HNMR δ ppm (CDCl$_3$): 5.18, 5.25 and 5.33 (each each s, each ArCHO—), 6.91–8.46 (30H, m, ArH), 8.49 (1H, s, Anthracene ring 9-H).

IR (KBr-disk) ν cm$^{-1}$: 1743 (COO—).

(4) Using 1,2,10-tris(4-benzyloxy-3-chlorobenzoyloxy)anthracene (280 mg, 0.4 mmole) obtained in above (3), the catalytic reduction was carried out in the same manner as described in Synthesis Example 1, (4) to afford 0.2 g of 1,2,10-tris(3-chloro-4-hydroxybenzoyloxy)anthracene as white crystals having a m.p. of 238° C.

$^1$HNMR δ ppm (Acetone-d$_6$): 6.98–8.41 (15H, m, ArH), 8.52 (1H, s, Anthracene ring 9-H), 10.41 (3H, bs, OH×3).

IR (KBr-disk) ν cm$^{-1}$: 3382 (OH), 1747 (COO—).

SYNTHESIS EXAMPLE 11

Synthesis of 1,2,10-tris(3-hydroxy-4-methylbenzoyloxy)anthracene (1) Using 3-hydroxy-3-methylbebnzoic acid (20.3 g, 0.13 mole) and benzyl chloride (50.8 g, 0.40 mole), the reaction was carried out in the same manner as described in Synthesis Example 1, (1). The crude solid was recrystallized from ethanol to give 15.0 g of 3-benzyloxy-4-methylbenzoic acid as white crystals having a m.p. of 159°–161° C.

$^1$HNMR δ ppm (DMSO-d$_6$): 2.26 (3H, s, CH$_3$), 5.18 (2H, a, ArCH$_2$O—), 7.27–7.43 (6H, m, ArH and Phenyl ring 5-H), 7.47 (1H, s, Phenyl ring 2-H), 7.51 (1H, d, J=7.7 Hz, Phenyl ring 6-H), 12.81 (1H, bs, COOH).

IR (KBr-disk) ν cm$^{-1}$: 1690 (COOH).

(2) Using 3-benzyloxy-4-methylbenzoic acid (3.0 g, 12.4 mmole) obtained in above (1), the reaction was carried out in the same manner as described in Synthesis Example 1, (2) to give 3.12 g of 3-benzyloxy-4-methylbenzoyl chloride as pale yellow crystals having a melting point of 49°–51° C.

IR (KBr-disk) ν cm$^{-1}$: 1741 (C=O).

(3) Using 3-benzoyl-4-methylbenzoyl chloride (2.85 g, 10.9 mmole) obtained in above (2) and 1,2-dihydroxy-10-anthrone (0.75 g, 3.3 mmole), the reaction was carried out in the same manner as described in Synthesis Example 1, (3), and the residue was chromatographed on silica gel (Wakogel C-200) with methylene chloride as eluent to give 160 mg of 1,2,10-tris(3-benzyloxy-4-methylbenzoyloxy)anthracene as yellow crystals having a melting point of 132°–135° C.

$^1$HNMR δ ppm (CDCl$_3$): 2.17, 2.27 and 2.31 (each 3H, each s, each CH$_3$), 5.03, 5.15 and 5.24 (each 2H, each s, each ArCH$_2$O—), 7.15–8.07 (30H, m, ArH), 8.45 (1H, s, Anthracene ring 9-H).

IR (KBr-disk) ν cm$^{-1}$: 1737 (COO—).

(4) Using 1,2,10-tris(3-benzyloxy-4-methylbenzoyloxy)anthracene (150 mg, 0.17 mmole) obtained in above (3), the catalytic reduction was carried out in the same manner as described in Synthesis Example 1, (4) to give 80 mg of 1,2,10-tris(3-hydroxy-4-methylbenzoyloxy)anthracene as white crystals having a m.p. of 251° C. (decomp.).

$^1$HNMR δ ppm (Acetone-d$_6$): 2.22, 2,25 and 2.27 (each 3H, each s, each CH$_3$), 6.95–8.26 (15H, m, ArH), 8.56 (1H, s, Anthracene ring 9-H), 10.11 (3H, bs, OH×3).

IR (KBr-disk) ν cm$^{-1}$: 3409 (OH), 1716 (COO—).

SYNTHESIS EXAMPLE 12

Synthesis of poly(methyl methacrylate/glycidyl methacrylate/2,3-dihydroxypropyl methacrylate)

(1) To a solution of methyl methacrylate (50.1 g, 0.5 mole) and glycidyl methacrylate (28.4 g, 0.2 mole) in toluene (240 ml), 2,2'-azobis(methyl 2-methylpropionate) (0.8 g)

was added, then the mixture was reacted with stirring at 80° C. for 7 hours under nitrogen. After cooling, the reaction mixture was poured into methanol (200 ml) and the polymer was precipitated. The polymer was filtered and dried under reduced pressure to give 77 g of poly (methyl methacrylate/glycidyl methacrylate) as white powders having $\overline{Mw}$ 35800 and $\overline{Mn}$ 19200 (GPC with polystyrene calibration). The composition of the polymer was found to be methyl methacrylate unit and glycidyl methacrylate unit in molar ratio of ca. 5:2 based on $^1$HNMR analysis.

(2) To a solution of poly(methyl methacrylate/glycidyl methacrylate) (5 g) obtained in above (1) in tetrahydrofuran (50 ml), 1N sulfuric acid (10 ml) was added. The mixture was reacted with stirring at 40° C. for 1 hour, cooled to 10° C. and poured into $H_2O$ (500 ml). The precipitate was filtered, washed with $H_2O$ and dried under reduced pressure to afford 2.5 g of poly(methyl methacrylate/glycidyl methacrylate/2,3-dihydroxypropyl methacrylate) as white powders having $\overline{Mw}$ 36300 and $\overline{Mn}$ 20200 (GPC with polystyrene calibration). The composition of the polymer was found to be methyl methacrylate unit and glycidyl methacrylate unit and 2,3-dihydroxypropyl methacrylate unit in molar ratio of ca. 5:1:1 based on $^1$HNMR analysis.

SYNTHESIS EXAMPLE 13

Synthesis of sorbitolpolyglycidylether/ ethylenediamine resin

A solution of sorbitolpolyglycidylether (9.1 g) and ethylenediamine (0.2 g) in 1,4-dioxane (15 ml) was reacted with stirring at 100° C. for 3 hours. After cooling, the reaction mixture was washed twice with (150 ml) and evaporated under reduced pressure to afford 2.3 g of sorbitolpolyglycidylether/ethylenediamine resin as a colorless viscous oil.

SYNTHESIS EXAMPLE 14

Synthesis of sorbitolpolyglycidylether/glutaric acid resin

A suspension of sorbitolpolyglycidylether (9.1 g), glutaric acid (0.8 g) and benzyltriethylammonium chloride (30 mg) was reacted with stirring at 80° C. for 4 hours. After cooling, the reaction mixture was diluted with methylene chloride (60 ml), washed with $H_2O$ (30 ml×3) and evaporated under reduced pressure to give 9.4 g of sorbitolpolyglycidylether/ glutaric acid resin as a pale yellow viscous oil.

SYNTHESIS EXAMPLE 15

Synthesis of poly(methyl methacrylate/glycidyl methacrylate/tert-butyl methacrylate)

Using methyl methacrylate (40.0 g, 0.4 mole), glycidyl methacrylate (28.4 g, 0.2 mole) and tert-butyl methacrylate (14.2 g, 0.1 mole), the polymerization was carried out in the same manner as described in Synthesis Example 12, (1), and the precipitate was filtered and dried under reduced pressure to give 78.5 g of poly(methyl methacrylate/glycidyl methacrylate/tert-butyl methacrylate) as white powders having $\overline{Mw}$ 35000 and $\overline{Mn}$ 19000 (GPC with polystyrene calibration). The composition of the polymer was found to be methyl methacrylate unit and glycidyl methacrylate unit and tert-butyl methacrylate unit in molar ratio of ca. 4:2:1 based on $^1$HNMR analysis.

SYNTHESIS EXAMPLE 16

Synthesis of poly(methyl methacrylate/glycidyl methacrylate/2-hydroxyethyl methacrylate)

Using methyl methacrylate (35.0 g, 0.35 mole), glycidyl methacrylate (28.4 g, 0.2 mole) and 2-hydroxyethyl methacrylate (13.0 g, 0.1 mole), the polymerization was carried out in the same manner as described in Synthesis Example 12, (1), and the precipitate was filtered and dried under reduced pressure to give 70.3 g of poly(methyl methacrylate/glycidyl methacrylate/2-hydroxyethyl methacrylate) as white powders having $\overline{Mw}$ 35000 and $\overline{Mn}$ 192000 (GPC with polystyrene calibration).

SYNTHESIS EXAMPLE 17

Synthesis of poly(methyl methacrylate/glycidyl methacrylate/n-butyl methacrylate)

Using methyl methacrylate (20.0 g, 0.2 mole), glycidyl methacrylate (14.2 g, 0.1 mole) and n-butyl methacrylate (7.1 g, 0.05 mole), the polymerization was carried out. in the same manner as described in Synthesis Example 12, (1), and the precipitate was filtered and dried under reduced pressure to afford 31.7 g of poly(methyl methacrylate/glycidyl methacrylate/n-butyl methacrylate) as white powders having $\overline{Mw}$ 35000 and $\overline{Mn}$ 19200 (GPC with polystyrene calibration). The composition of the polymer was found to be methyl methacrylate unit and glycidyl methacrylate unit and n-butyl methacrylate unit in molar ratio of ca. 4:2:1 based on $^1$HNMR analysis.

SYNTHESIS EXAMPLE 18

Synthesis of poly(methyl methacrylate/glycidyl methacrylate/9-anthracenemethyl methacrylate)

(1) To a suspension of 9-anthracenemethanol (50 g, 0.24 mole) in triethylamine (50.6 g, 0.5 mole) and benzene (750 ml), a solution of methacryloyl chloride (52.3 g, 0.5 mole) in benzene (50 ml) was added dropwise at 10° C. or below, continued to stir at 20° C. for 1 hour and allowed to stand at room temperature overnight. The reaction mixture was poured into ethyl acetate (150 ml) and $H_2O$ (800 ml). The organic layer was washed 1.4% $Na_2CO_3$ aq. (700 ml×l), then $H_2O$ (1 l×4) and evaporated under reduced pressure. The residual oil was crystallized from cyclohexane to afford 74.0 g of 9-anthracenemethyl methacrylate as yellow crystals having a m.p. of 83°–84° C.

$^1$HNMR δ ppm (CDCl$_3$): 1.90 (3H, s, C$\underline{H}_3$), 5.48 (1H, s, C=C$\underline{H}_2$), 6.04 (1H, s, C=C$\underline{H}_2$), 6.19 (2H, a, ArCH$_2$O—), 7.43–8.39 (8H, m, Anthracene ring), 8.46 (1H, s, Anthracene ring 10-H).

IR (KBr-disk) vcm$^{-1}$: 1722 (COO—).

(2) Using methyl methacrylate (20.0 g, 0.20 mole), glycidyl methacrylate (14.2 g 0.10 mole) and 9-anthracenemethyl methacrylate (8.3 g, 0.03 mole) obtained in above (1), the polymerization was carried out in the same manner as described in Synthesis Example 12, (1). The precipitate was filtered and dried under reduced pressure to afford 30.8 g of poly(methyl methacrylate/glycidyl methacrylate/9-anthracenemethyl methacrylate) as pale yellow powders having $\overline{Mw}$ 37500 and $\overline{Mn}$ 19000 (GPC with polystyrene calibration). The composition of the polymer was found to be methyl methacrylate unit and glycidyl methacrylate unit and 9-anthracenemethyl methacrylate unit in molar ratio of ca. 20:10:3 based on $^1$HNMR analysis.

SYNTHESIS EXAMPLE 19

Synthesis of poly(methyl acrylate/glycidyl methacrylate)

Using methyl acrylate (21.5 g, 0.25 mole) and glycidyl methacrylate (14.2 g, 0.10 mole), the polymerization was carried out in the same manner as described in Synthesis Example 12, (1). The precipitate was filtered and dried under reduced pressure to give 21.0 g of poly(methyl acrylate/glycidylmethacrylate) as a colorless viscous oil having $\overline{M}w$ 35000 and $\overline{M}n$ 18000 (GPC with polystyrene calibration). The composition of the polymer was found to be methyl acrylate unit and glycidyl methacrylate unit in molar ratio of ca. 5:2 based on $^1$HNMR analysis.

Example 1

A deep ultraviolet absorbent of the following composition was prepared:

| | |
|---|---|
| Poly(methyl methacrylate/glycidyl methacrylate/2,3-dihydroxypropyl methacrylate) (resin of Synthesis Example 12) | 4.0 g |
| 2,6,9-tris(4-hydroxybenzoyloxy)anthracene (compound of Synthesis Example 1) | 1.0 g |
| Tetrahydrofurfuryl alcohol | 45.0 g |
| Propylene glycol monomethyl ether acetate | 50.0 g |

The above composition was spin coated on a substrate (silicon wafer) and baked on a hot plate at 200° C. for 90 seconds to form a 100 nm thick deep ultraviolet absorbent film (antireflection coating). This film was subjected to UV measurements. A UV spectrum of the film is shown in FIG. 1.

The spectrum of FIG. 1 shows light absorption of this film at around 250 nm.

The deep ultraviolet absorbent film was not dissolved in acetone at all. This showed that crosslinking reaction took place.

Example 2

A deep ultraviolet absorbent of the following composition was prepared:

| | |
|---|---|
| Poly(methyl methacrylate/glycidyl methacrylate/2,3-dihydroxypropyl methacrylate) (resin of Synthesis Example 12) | 4.0 g |
| 1,2,10-tris(4-hydroxybenzene-sulfonyloxy)anthracene (compound of Synthesis Example 6) | 1.0 g |
| Tetrahydrofurfuryl alcohol | 45.0 g |
| Propylene glycol monomethyl ether acetate | 50.0 g |

Figure 2:
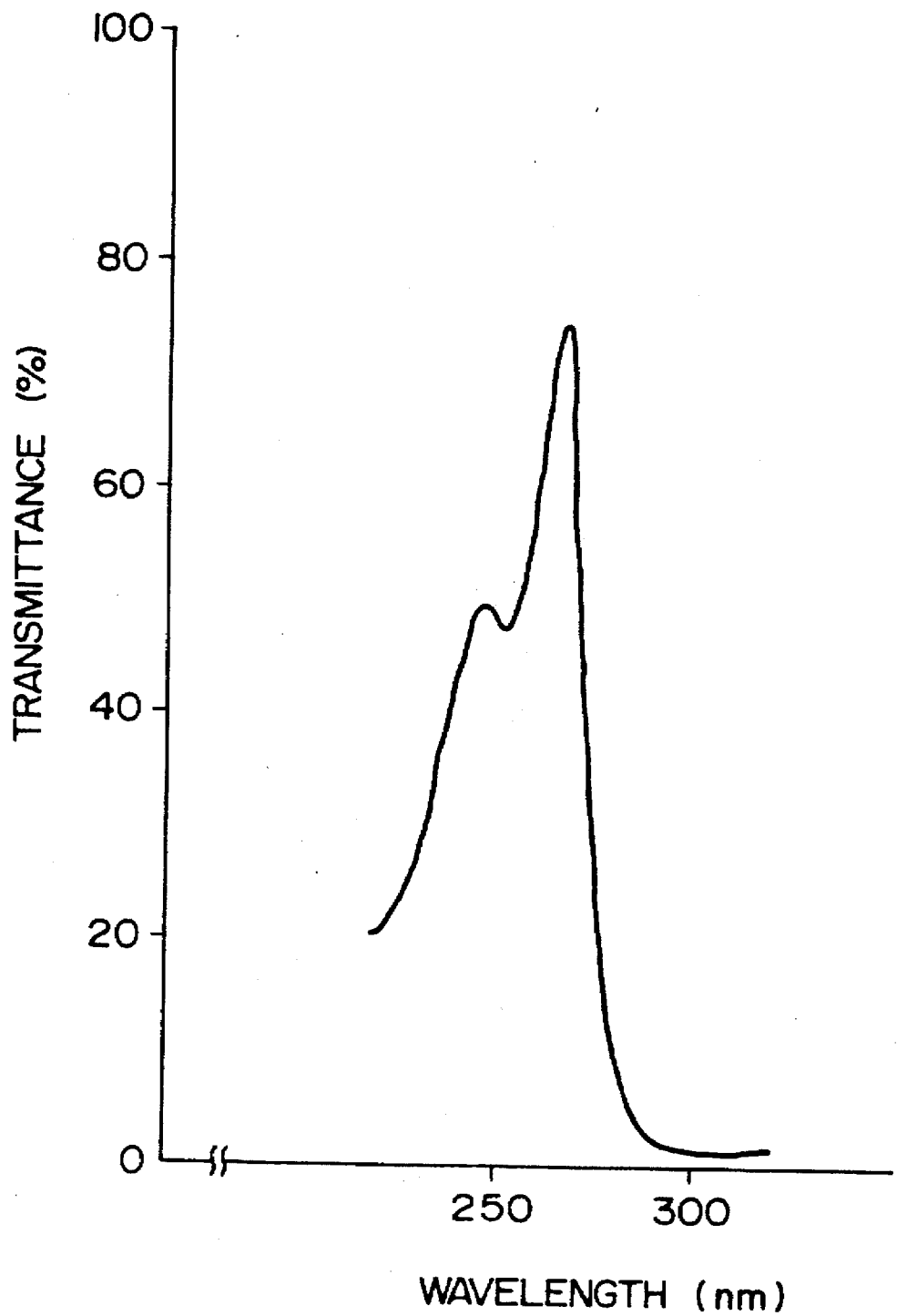
FIG. 2 is an ultraviolet spectrophotometric curve of the deep ultraviolet absorbent film obtained in Example 2.

The above composition was spin coated on a substrate (silicon wafer) and baked on a hot plate at 180° C. for 90 seconds to form a 100 nm thick deep ultraviolet absorbent film. This film was subjected to UV measurements. A UV spectrum of this film is shown in FIG. 2. The spectrum shows light absorption of this film at around 250 nm.

The deep ultraviolet absorbent film was not dissolved in acetone at all. This showed that crosslinking reaction took place.

Example 3

A chemically amplified positive resist of the following composition was prepared:

| | |
|---|---|
| Poly[p-(1-ethoxyethoxy)styrene/p-hydroxystyrene] | 2.50 g |
| 2-cyclohexylcarbonyl-2-(p-toluenesulfonyl)propane | 0.13 g |
| Propylene glycol monomethyl ether acetate | 7.37 g |

A pattern was formed on a highly reflective substrate non-uniform in thickness by using the above chemically amplified positive resist and the deep ultraviolet absorbent of Example 1. The result is discussed below with reference to FIG. 3.

Figure 3A:
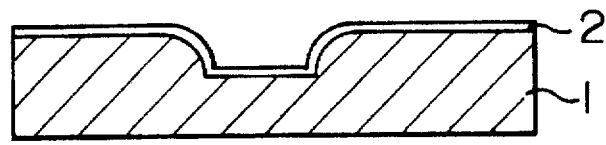
FIGS. 3(A) to 3(E) are sectional views illustrating the pattern forming process according to Example 3 where the deep ultraviolet absorbent of this invention was used as undercoat.
Figure 3B:
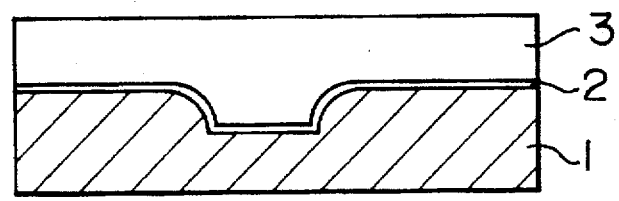
Figure 3B:
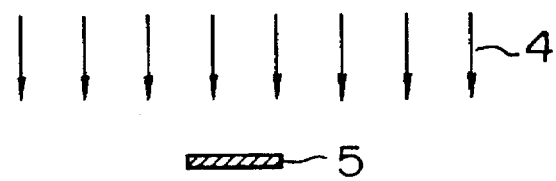
Figure 3C:
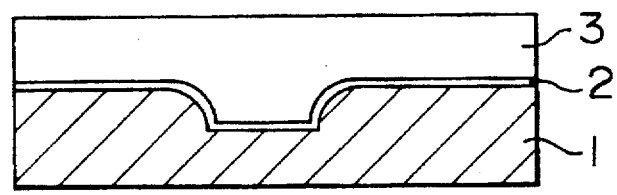
Figure 3D:
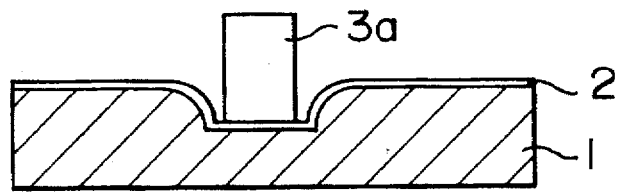
Figure 3E:
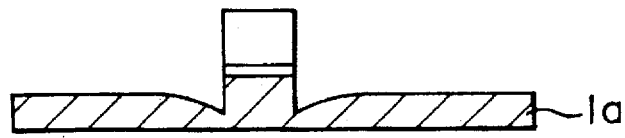

A deep ultraviolet absorbent 2 of the composition described in Example 1 was spin coated on a high-reflectance aluminum topographic substrate 1 obtained by subjecting a silicon substrate to photolithography, etching and aluminum sputtering and hot plate baked at 200° C. for 90 seconds to form a deep ultraviolet absorbent film having a thickness of 100 nm (FIG. 3A). On this absorbent film was spin coated a chemically amplified positive resist 3 of the above composition, followed by hot plate baking at 90° C. for 90 seconds to form a 1.0 µm thick resist film (FIG. 3B). Then the film was selectively exposed to excimer laser light 4 of 248.4 nm through a mask 5 (FIG. 3C). After hot plate post-baking at 100° C. for 90 seconds, the film was developed with an alkaline developing solution (a 2.38% tetramethylammonium hydroxide solution), whereby the exposed portion alone of the resist 3 was dissolved away to give a positive pattern 3a (FIG. 3D). This positive pattern could resolve the 0.25 µm lines and spaces and had a good shape (rectangular). Exposure to the film was approximately 30 mJ/cm$^2$. Then, with the pattern 3a serving as a mask, the deep ultraviolet absorbent film 2 according to this invention and the aluminum substrate 1 were etched with oxygen gas and chlorine type gas successively (FIG. 3E). The consequently formed etching pattern 1a had absolutely no dimensional variation from the resist pattern 3a and thus was a quite satisfactory pattern.

Examples 4–25

The deep ultraviolet absorbents of the compositions shown in Tables 1–7 below were prepared.

TABLE 1

| | | |
|---|---|---|
| Example 4 | Poly(methyl methacrylate/glycidyl methacrylate/2,3-dihydroxypropyl methacrylate) | 4.0 g |
| | 1,2,10-tris(4-hydroxybenzene-sulfonyloxy)anthracene | 1.0 g |
| | Tetrahydrofurfuryl alcohol | 45.0 g |
| | Propylene glycol monomethyl ether acetate | 50.0 g |
| Example 5 | Srbitol polyglycidyl ether/ethylenediamine resin (resin of Synthesis Example 13) | 3.0 g |
| | Poly(methyl methacrylate/glycidyl methacrylate/2,3-dihydroxypropyl methacrylate) | 1.0 g |
| | 1,5,9-tris(4-hydroxybenzene-sulfonyloxy)anthracene (compound of Synthesis Example 7) | 1.0 g |
| | Tetrahydrofurfuryl alcohol | 45.0 g |
| | Propylene glycol monomethyl ether acetate | 50.0 g |
| Example 6 | Sorbitol polyglycidyl ether/ethylenediamine resin | 3.0 g |
| | Poly(methyl methyacrylate/glycidyl methacrylate/2,3-dihydroxypropyl | 1.0 g |

TABLE 1-continued

| | | |
|---|---|---|
| | methacrylate) | |
| | 1,5,9-tris(4-hydroxybenzoyloxy)-anthracene (compound of Synthesis Example 3) | 1.0 g |
| | Tetrahydrofurfuryl alcohol | 45.0 g |
| | Propylene glycol monomethyl ether acetate | 50.0 g |

TABLE 2

| | | |
|---|---|---|
| Example 7 | Sorbitol Polyglycidyl ether/ ethylenediamine resin | 3.0 g |
| | Poly(methyl methacrylate/glycidyl methacrylate/2,3-dihydroxypropyl methacrylate) | 1.0 g |
| | 2,6-bis(4-hydroxybenzoyloxy)-anthracene (compound of Synthesis Example 2) | 2.0 g |
| | Diethylene glycol dimethyl ether | 94.0 g |
| Example 8 | Sorbitol polyglycidyl ether/ethylene-diamine resin | 3.0 g |
| | Poly(methyl methacrylate/glycidyl methacrylate/2,3-dihydroxypropyl methacrylate) | 1.0 g |
| | 2,6,9-tris(4-hydroxybenzene-sulfonyloxy)anthracene (compound of Synthesis Example 8) | 2.0 g |
| | Diethylene glycol dimethyl ether | 94.0 g |
| Example 9 | Sorbitol polyglycidyl ether/glutaric acid resin (resin of Synthesis Example 14) | 3.0 g |
| | Poly(methyl methacrylate/glycidyl methacrylate/2,3-dihydroxypropyl methacrylate) | 1.0 g |
| | 1,5,9-tris(4-hydroxybenzoyloxy)-anthracene | 1.0 g |
| | Tetrahydrofurfuryl alcohol | 45.0 g |
| | Propylene glycol monomethyl ether acetate | 50.0 g |

TABLE 3

| | | |
|---|---|---|
| Example 10 | Sorbitol polyglycidyl ether/glutaric acid resin | 3.0 g |
| | Poly(methyl methacrylate/glycidyl methacrylate/2,3-dihydroxypropyl methacrylate) | 1.0 g |
| | 1,2,10-tris(4-hydroxybenzene-sulfonyloxy)anthracene | 1.0 g |
| | tetrahydrofurfuryl alcohol | 45.0 g |
| | Propylene glycol monomethyl ether acetate | 50.0 g |
| Example 11 | Sorbitol polyglycidyl ether/glutaric acid resin | 3.0 g |
| | Poly(methyl methacrylate/glycidyl methacrylate/2,3-dihydroxypropyl methacrylate) | 1.0 g |
| | 2,6,9-tris(4-hydroxy-3-methoxy-benzoyloxy)anthracene (compound of Synthesis Example 5) | 1.0 g |
| | Tetrahydrofurfuryl alcohol | 45.0 g |
| | Propylene glycol monomethyl ether acetate | 50.0 g |

TABLE 4

| | | |
|---|---|---|
| Example 12 | Poly(methyl methacrylate/glycidyl methacrylate/2,3-dihydroxypropyl methacrylate) | 5.5 g |
| | 1,5,9-tris(4-hydroxybenzene-sulfonyloxy)anthracene | 1.5 g |
| | Tetrahydrofurfuryl alcohol | 43.0 g |

TABLE 4-continued

| | | |
|---|---|---|
| | Propylene glycol monomethyl ether acetate | 50.0 g |
| Example 13 | Poly(methyl methacrylate/glycidyl methacrylate/2,3-hydroxypropyl methacrylate) | 5.5 g |
| | 1,2,10-tris(4-hydroxybenzoyloxy)-anthracene (compound of Synthesis Example 4) | 1.5 g |
| | Propylene glycol monomethyl ether acetate | 93.0 g |
| Example 14 | Poly(methyl methacrylate/glycidyl methacrylate) (resin of Synthesis Example 12 (1) | 4.0 g |
| | 1,2,10-tris(4-hydroxybenzene-sulfonyloxy)anthracene | 1.2 g |
| | Tetrahydrofurfuryl alcohol | 44.8 g |
| | Propylene glycol monomethyl ether acetate | 50.0 g |
| Example 15 | Poly(methyl methacrylate/glycidyl methacrylate) | 4.0 g |
| | 1,2,10-tris(4-hydroxybenzoyloxy)-anthracene | 2.0 g |
| | Propylene glycol monomethyl ether acetate | 75.0 g |
| | Ethyl lactate | 19.0 g |

TABLE 5

| | | |
|---|---|---|
| Example 16 | Poly(methyl methacrylate/glycidyl methacrylate/tert-butyl methacrylate) (resin of Synthesis Example 15) | 4.5 g |
| | 1,2,10-tris(4-hydroxybenzene-sulfonyloxy)anthracene | 1.2 g |
| | 9-anthracenemethanol | 0.3 g |
| | Propylene glycol monomethyl ether acetate | 60.0 g |
| | Ethyl lactate | 34.0 g |
| Example 17 | Poly(methyl methacrylate/glycidyl methacrylate/2-hydroxyethyl methacrylate) (resin of Synthesis Example 16) | 4.0 g |
| | 1,5,9-tris(4-hydroxybenzene-sulfonyloxy)anthracene | 1.2 g |
| | 9-(2-methoxyethoxy)methylanthracene | 0.3 g |
| | Propylene glycol monomethyl ether acetate | 50.0 g |
| | Ethyl lactate | 44.5 g |
| Example 18 | Poly(meth,yl methacrylate/glycidyl methacrylate/n-butyl methacrylate) (resin of Synthesis Example 17) | 4.0 g |
| | 2,6,9-tris(3,4-dihydroxybenzoyloxy)-anthracene (compound of Synthesis Example 9) | 2.0 g |
| | Propylene glycol monomethyl ether acetate | 75.0 g |
| | Ethyl lactate | 19.0 g |

TABLE 6

| | | |
|---|---|---|
| Example 19 | Poly(methyl methacrylate/glycidyl methacrylate/tert-butyl methacrylate) | 4.0 g |
| | 1,2,10-tris(3-chloro-4-hydroxy-benzoyloxy)anthracene (compound of Synthesis Example 10) | 2.0 g |
| | Methyl 3-methoxypropionate | 15.0 g |
| | Propylene glycol monomethyl ether acetate | 79.0 g |
| Example 20 | Poly(methyl methacrylate/glycidyl methacrylate) | 4.0 g |
| | 1,2,10-tris(4-hydroxybenzoyloxy)-anthracene | 2.0 g |
| | 1,2,10-triacetoxyanthracene | 0.3 g |
| | Propylene glycol monomethyl ether acetate | 78.7 g |

TABLE 6-continued

| | | |
|---|---|---|
| Example 21 | Ethyl lactate | 15.0 g |
| | Poly(methyl methacrylate/glycidyl methacrylate/2,3-dihydroxypropyl methacrylate) | 4.0 g |
| | 1,2,10-tris(3-hydroxy-4-methyl-benzoyloxy)anthracene (compound of Synthesis Example 11) | 94.0 g |
| | Ethyl lactate | 94.0 g |
| Example 22 | Poly(methyl methacrylate/glycidyl methyacrylate/9-anthracenemethyl methacrylate (resin of Synthesis Example 18) | 4.5 g |
| | 1,2,10-tris(4-hydroxybenzoyloxy)-anthracene | 2.0 g |
| | Propylene glycol monomethyl ether acetate | 79.0 g |
| | Ethyl lactate | 14.5 g |

TABLE 7

| | | |
|---|---|---|
| Example 23 | Poly(methyl methacrylate/glycidyl methacrylate/n-butyl methacrylate) | 4.0 g |
| | 2,6,9-tris(4-hydroxy-3-methoxy-benzoyloxy)anthracene | 2.0 g |
| | propylene glycol monomethyl ether acetate | 79.0 g |
| | Ethyl lactate | 15.0 g |
| Example 24 | Poly(methyl methacrylate/glycidyl methacrylate/tert-butyl methacrylate) | 4.5 g |
| | 2,6-bis(4-hydroxybenzoyloxy)-9-methoxyanthracene (compound of Synthesis Example 12) | 2.0 g |
| | 1,5,9-triacetoxyanthracene | 0.3 g |
| | Propylene glycol monomethyl ether acetate | 73.2 g |
| | Butyl lactate | 20.0 g |
| Example 25 | Poly(methyl acrylate/glycidyl methacrylate) (resin of Synthesis Example 19) | 4.0 g |
| | 1,5,9-tris(4-hydroxybenzoyloxy)-anthracene | 2.0 g |
| | Tetrahydrofurfuryl alcohol | 40.0 g |
| | Propylene glycol monomethyl ether acetate | 54.0 g |

By using the deep ultraviolet absorbents of the compositions shown in Tables 1–7, the absorbent films were formed according to the procedure of Example 3, and a pattern was formed on each of said films in the same way as Example 3 by using the chemically amplified positive resist described in Example 3. The results are shown in Tables 8 and 9.

TABLE 8

| Example | Crosslinking conditions | Exposure | 0.25 μm pattern | Halation |
|---|---|---|---|---|
| 4 | 180° C., 90 sec. | 30 mJ/cm$^2$ | Good form | Showed preventive effect |
| 5 | 220° C., 90 sec. | 28 mJ/cm$^2$ | " | Showed preventive effect |
| 6 | 220° C., 90 sec. | 30 mJ/cm$^2$ | " | Showed preventive effect |
| 7 | 220° C., 90 sec. | 28 mJ/cm$^2$ | " | Showed preventive effect |
| 8 | 220° C., 90 sec. | 28 mJ/cm$^2$ | " | Showed preventive effect |
| 9 | 220° C., 90 sec. | 28 mJ/cm$^2$ | " | Showed preventive effect |
| 10 | 220° C., 90 sec. | 28 mJ/cm$^2$ | " | Showed preventive effect |
| 11 | 220° C., 90 sec. | 28 mJ/cm$^2$ | " | Showed preventive effect |

TABLE 8-continued

| Example | Crosslinking conditions | Exposure | 0.25 μm pattern | Halation |
|---|---|---|---|---|
| 12 | 180° C., 90 sec. | 28 mJ/cm$^2$ | " | Showed preventive effect |
| 13 | 200° C., 90 sec. | 30 mJ/cm$^2$ | " | Showed preventive effect |
| 14 | 180° C., 90 sec. | 28 mJ/cm$^2$ | " | Showed preventive effect |
| 15 | 200° C., 90 sec. | 30 mJ/cm$^2$ | " | Showed preventive effect |

TABLE 9

| Example | Crosslinking conditions | Exposure | 0.25 μm pattern | Halation |
|---|---|---|---|---|
| 16 | 180° C., 90 sec. | 30 mJ/cm$^2$ | Good form | Showed preventive effect |
| 17 | 180° C., 90 sec. | 30 mJ/cm$^2$ | " | Showed preventive effect |
| 18 | 200° C., 90 sec. | 28 mJ/cm$^2$ | " | Showed preventive effect |
| 19 | 200° C., 90 sec. | 28 mJ/cm$^2$ | " | Showed preventive effect |
| 20 | 200° C., 90 sec. | 28 mJ/cm$^2$ | " | Showed preventive effect |
| 21 | 200° C., 90 sec. | 30 mJ/cm$^2$ | " | Showed preventive effect |
| 22 | 200° C., 90 sec. | 28 mJ/cm$^2$ | " | Showed preventive effect |
| 23 | 200° C., 90 sec. | 30 mJ/cm$^2$ | " | Showed preventive effect |
| 24 | 200° C., 90 sec. | 28 mJ/cm$^2$ | " | Showed preventive effect |
| 25 | 200° C., 90 sec. | 30 mJ/cm$^2$ | " | Showed preventive effect |

As is clear from the results in Tables 8 and 9, the ultraviolet absorbent films obtained in Examples to 25 were not dissolved in acetone at all. This means that the crosslinking reaction took place.

Comparative Example 1

By using a chemically amplified positive resist of the composition described in Example 3 but without using the deep ultraviolet absorbent of the present invention, a pattern was formed on an aluminum substrate of non-uniform in thickness in the same way as Example 3.

Figure 4A:
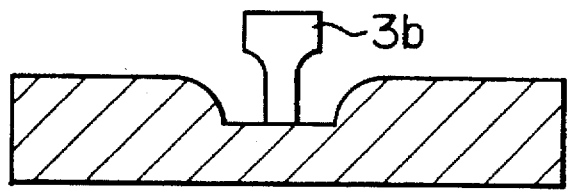
FIGS. 4(A) and 4(B) are sectional views observed in Comparative Example 1 where it was tried to form a pattern without using the deep ultraviolet absorbent of this invention but it was impossible to form the desired pattern.
Figure 4B:
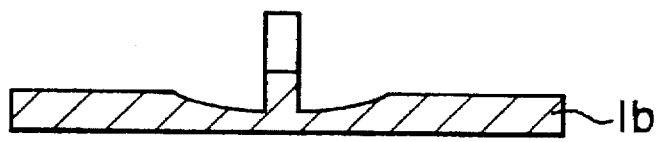

The formed pattern 3b, as shown in FIG. 4A, was a defective pattern which has been affected by reflection of light. Thereafter, it was tried to etch the substrate, but because of the defective resist pattern, the etching pattern (1b) had a sizable dimensional variation from the initial resist pattern (FIG. 4B).

Comparative Examples 2–5

The deep ultraviolet absorbents of the compositions shown in Table 10 were prepared.

TABLE 10

| | | |
|---|---|---|
| Comp. Example 2 | Poly(methyl methacrylate/glycidyl methacrylate/2,3-hydroxypropyl methacrylate) | 4.0 g |
| | Tetrahydrofurfuryl alcohol | 45.0 g |
| | Propylene glycol monomethyl ether acetate | 50.0 g |

TABLE 10-continued

| Comp. Example 3 | Sorbitol polyglycidyl ether/ ethylenediamine resin | 3.0 g |
|---|---|---|
| | Poly(methyl methacrylate/glycidyl methacrylate/2,3-dihydroxypropyl methacrylate) | 1.0 g |
| | Diethylene glycol dimethyl ether | 94.0 9 |
| Comp. Example 4 | Poly(methyl methacrylate/glycidyl methacrylate) | 4.0 g |
| | 1,2,10-triacetoxyanthracene | 0.3 g |
| | Propylene glycol monomethyl ether acetate | 78.7 g |
| | Ethyl lactate | 15.0 g |
| Comp. Example 5 | Poly(methyl methacrylate/glycidyl methacrylate/tert-butyl methacrylate) | 4.5 g |
| | 9-anthracenemethanol | 0.3 g |
| | Propylene glycol monomethyl ether acetate | 60.0 g |
| | Ethyl lactate | 34.0 g |

Figure 5:
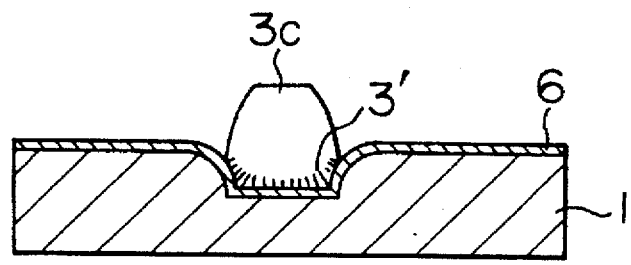
FIG. 5 is a sectional view observed when it was tried to form a pattern by using the materials of Comparative Examples 2–5 as undercoat, it being found unable to form the desired pattern.

The absorbent films were formed in the same way as Example 3 by using the deep ultraviolet absorbents of the compositions shown in Table 10 in place of the absorbent of the present invention. A pattern was formed on each of said films in the same way as Example 3 by using the chemically amplified positive resist of the composition described in Example 3. Any of the patterns formed was very bad in form as shown in FIG. 5 due to intermixture of the absorbent with the resist material at the interface.

Comparative Example 6

A film forming material having the following composition was prepared:

| Poly(methyl methacrylate/glycidyl methacrylate/2,3-dihydroxypropyl methacrylate) [resin of Synthesis Example 12] | 4.0 g |
|---|---|
| 1,8,9-Tris(4-hydroxybenzoyloxy)anthracene [compound disclosed in DE-OS 2,257,442] | 1.0 g |
| Tetrahydrofurfuryl alcohol | 45.0 g |
| Propylene glycol monomethyl ether acetate | 50.0 g |

The above-mentioned composition was spin coated on a substrate (silicon wafer) and baked at 200° C. for 90 seconds by a hot plate to give an absorbent film of 100 nm thick. When the absorbent film was immersed in acetone, it was easily dissolved.

This means that when 1,8,9-tris(4-hydroxybenzoyloxy) anthracene is used, no crosslinking reaction proceeds, resulting in failing to obtain a deep ultraviolet absorbent film applying crosslinking reaction.

As mentioned above, it was confirmed that use of a resin composition alone or further incorporation of an ordinary deep ultraviolet absorbent is practically ineffective and that addition of a deep ultraviolet absorbent composition capable of crosslinking reaction according to the present invention is essential for obtaining the desired effect.

As is apparent from the foregoing description, when a deep ultraviolet absorbent according to the present invention is used as undercoating material of the resist for exposure with such light as deep ultraviolet light (300 nm or less), KrF excimer laser light (248.4 nm) or ArF excimer laser light (193 nm) and applied to a high-reflectance substrate or topographic substrate made of aluminum, alumium/silicon, aluminum/silicon/copper, polysilicon, copper, silver or the like, it is possible to obtain a good pattern form with a size of a quarter of a micron order while maintaining high resolving performance and high sensitivity without causing notching or halation that can lead to troubles such as disconnection of the substrate. Thus, the present invention is of great value for formation of ultra-fine patterns in semiconductor industries.

What is claimed is:

1. A process for forming a pattern on a semiconductor substrate which comprises:

(i) coating the substrate with a deep ultraviolet absorbent composition;

(ii) heating the coating to bring about a crosslinking reaction, thereby forming a film on said substrate;

(iii) coating a resist material on said film;

(iv) baking the coating of the resist material on said film to form a resist film;

(v) exposing the resist film to KrF excimer laser light or deep ultraviolet light through a mask;

(vi) heating the exposed film; and (vii) developing the heated and exposed film with an alkaline developing solution;

wherein the deep ultraviolet absorbent composition comprises a) at least one compound containing one or more glycidyl groups, b) at least one anthracene compound, and c) a solvent capable of dissolving said compounds; and wherein said at least one anthracene compound is a compound of formula [1]

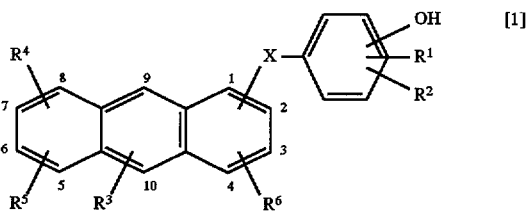

wherein X represents —O—SO$_2$—, —O—CO— or —CO—; R$^1$ and R$^2$ represent independently a hydrogen atom, an alkyl group, an alkoxyl group, a halogen atom or a hydroxyl group; R$^3$, R$^4$, R$^5$ and R$^6$ represent independently a hydrogen atom, an alkyl group, an alkoxy group, a halogen atom or a group of formula [2]

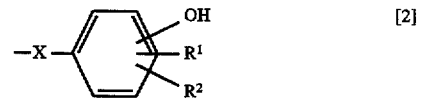

wherein X, R$^1$ and R$^2$ are as defined above; provided that at least one of R$^3$ through R$^6$ is a group of formula [2], and further provided that groups of formula [2] cannot be present at the 1, 8, and 9 positions of the anthracene ring at the same time.

2. A process for forming a pattern according to claim 1, wherein X in formula [1] is —O—CO— and X in formula [2] is —O—CO—.

3. A process for forming a pattern according to claim 1, wherein X in formula [1] is —O—SO$_2$— and X in formula [2] is —O—SO$_2$—.

4. A process for forming a pattern according to claim 1, wherein at least one hydroxyl group in formulas [1] and [2] is para or meta to X.

* * * * *